(12) United States Patent
Wong et al.

(10) Patent No.: US 9,228,005 B2
(45) Date of Patent: Jan. 5, 2016

(54) MYONECTIN (CTRP15), COMPOSITIONS COMPRISING SAME, AND METHODS OF USE

(71) Applicant: THE JOHNS HOPKINS UNIVERSITY, Baltimore, MD (US)

(72) Inventors: Guang William Wong, Lutherville, MD (US); Marcus Michael Seldin, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/373,685

(22) PCT Filed: Jan. 24, 2013

(86) PCT No.: PCT/US2013/022855
§ 371 (c)(1),
(2) Date: Jul. 22, 2014

(87) PCT Pub. No.: WO2013/112663
PCT Pub. Date: Aug. 1, 2013

(65) Prior Publication Data
US 2014/0371142 A1    Dec. 18, 2014

Related U.S. Application Data

(60) Provisional application No. 61/590,940, filed on Jan. 26, 2012.

(51) Int. Cl.
| | | |
|---|---|---|
| *A61K 38/00* | (2006.01) | |
| *A61P 3/06* | (2006.01) | |
| *A61K 38/16* | (2006.01) | |
| *C07K 1/00* | (2006.01) | |
| *C07K 14/00* | (2006.01) | |
| *C07K 17/00* | (2006.01) | |
| *C07K 14/52* | (2006.01) | |
| *C07K 14/775* | (2006.01) | |
| *A61K 38/17* | (2006.01) | |
| *C07K 14/47* | (2006.01) | |
| *C07K 16/24* | (2006.01) | |

(52) U.S. Cl.
CPC .............. *C07K 14/52* (2013.01); *A61K 38/1709* (2013.01); *C07K 14/47* (2013.01); *C07K 14/775* (2013.01); *C07K 16/24* (2013.01); *A61K 38/00* (2013.01); *C07K 2317/76* (2013.01)

(58) Field of Classification Search
None
See application file for complete search history.

(56) References Cited

U.S. PATENT DOCUMENTS

2005/0266464 A1    12/2005    Marshall et al.

FOREIGN PATENT DOCUMENTS

| WO | 2008048057 A1 | 4/2008 |
|---|---|---|
| WO | 2009076359 A2 | 6/2009 |

OTHER PUBLICATIONS

Zheng et al., Arterioscler. Thromb. Vasc. Biol. 31:2616-2623 (2011).*
Pedersen, B., "Muscles and their myokines", J. Exp. Biol., Jan. 15, 2011, vol. 214, pp. 337-346.
Seldin, M., et al., "Myonectin (CTRP15), a novel myokine that links skeletal muscle to systemic lipid homeostasis", J. Biol. Chem., Feb. 17, 2012, vol. 287, No. 15, pp. 11968-11980.

* cited by examiner

*Primary Examiner* — James H Alstrum Acevedo
*Assistant Examiner* — Thea D'Ambrosio
(74) *Attorney, Agent, or Firm* — Johns Hopkins Technology Transfer

(57) ABSTRACT

Disclosed is the novel myokine known as myonectin (CTRP15), an isolated nucleic acid encoding the myonectin (CTRP15) gene, and the amino acid sequence encoding the myonectin (CTRP15) protein. Methods of isolation of the nucleic acid, protein, polypeptides and methods of making antibodies to the myonectin (CTRP15) protein are provided. The use of myonectin (CTRP15) in the modulation of lipid and/or glucose metabolism, suppressing the expression of autophagy genes, inhibiting LC3 lipidation and autophagosome-dependent p62 degradation, and activating the Akt/mTOR pathway is also provided.

2 Claims, 16 Drawing Sheets

MYONECTIN (CTRP15), COMPOSITIONS COMPRISING SAME, AND METHODS OF USE

CROSS-REFERENCE TO RELATED APPLICATIONS

This application is a 35 U.S.C. §371 U.S. national entry of International Application PCT/US2013/022855 having an international filing date of Jan. 24, 2013, which claims the benefit of U.S. Provisional Application No. 61/590,940, filed Jan. 26, 2013, the content of each of the aforementioned applications is herein incorporated by reference in their entirety.

STATEMENT OF GOVERNMENTAL INTEREST

This invention was made with government support under grant nos. DK008417, DK084607 and DK007751 awarded by the National Institutes of Health. The government has certain rights in the invention.

INCORPORATION-BY-REFERENCE OF MATERIAL SUBMITTED ELECTRONICALLY

This application contains a sequence listing. It has been submitted electronically via EFS-Web as an ASCII text file entitled "P11853-02_ST25". The sequence listing is 12,511 bytes in size, and was created on Jan. 23, 2013. It is hereby incorporated by reference in its entirety.

BACKGROUND OF THE INVENTION

A large proportion of diet-derived glucose is taken up by skeletal muscle in response to insulin, and excess glucose is stored in muscle as glycogen until mobilized. In addition, muscle burns large amounts of fat via mitochondrial β-oxidation in response to energy demands. Insulin resistance in skeletal muscle has long been recognized to be an important underlying mechanism of type 2 diabetes. While the importance of skeletal muscle in controlling whole-body glucose and lipid metabolism is well established, its role as an endocrine tissue that secretes biologically active polypeptide hormones and cytokines (collectively termed myokines) involved in modulating metabolic, inflammatory, and other physiological processes in non-muscle tissues has only recently been investigated.

Recent proteomics studies focusing on the secretome (the entire complement of secreted proteins) of cultured mouse or human myotubes have revealed a large number (~250 in human and ~600 in mouse) of muscle cell-derived secretory proteins with potential autocrine, paracrine, and/or endocrine functions. For example, IL-6, FGF-21, Insulin-like 6 (Insl6) follistatin-like 1 (Fstl-1; also known as TSC-36), LIF, IL-7, IL-15, and musclin are currently characterized as myokines. These myokines act locally in an autocrine/paracrine manner and/or as endocrine factors linking skeletal muscle to regulation of physiological processes in other tissues.

However, the expression of all myokines described to date is not restricted to skeletal muscle—they are generally expressed by a variety of cell types, and most are, in fact, expressed at much higher levels by non-muscle tissues. Prior to the present invention, no myokine has been discovered to be preferentially expressed by skeletal muscle.

Therefore, there still exists a need for compositions suitable for use in modulation of metabolic, inflammatory and whole-body fatty acid metabolism.

SUMMARY OF THE INVENTION

In accordance with an embodiment, the present invention provides the first molecular, biochemical, and functional characterization of a protein identified as myonectin (CTRP15), along with evidence that it is a novel nutrient-responsive myokine secreted by skeletal muscle to regulate whole-body fatty acid metabolism.

In accordance with an embodiment of the present invention, the myonectin (CTRP15) protein was identified as a novel myokine, e.g., a peptide having autocrine, paracrine and endocrine activity in skeletal muscle.

In accordance with another embodiment, the present invention provides an isolated polynucleotide encoding the myonectin (CTRP15) gene.

In accordance with a further embodiment, the present invention provides an isolated polynucleotide encoding the myonectin (CTRP15) gene, having the sequence of SEQ ID NO: 1.

In accordance with still a further embodiment, the present invention provides a recombinant expression vector comprising the isolated nucleotide sequence encoding the myonectin (CTRP15) gene.

In accordance with an embodiment, the present invention provides an isolated or purified myonectin CTRP15 protein.

In accordance with another embodiment, the present invention provides an isolated or purified polypeptide of myonectin (CTRP15), comprising the amino acid sequence of SEQ ID NO: 2, or a functional portion thereof.

In accordance with yet another embodiment, the present invention provides an isolated or purified nucleic acid comprising a nucleotide sequence which is complementary to the nucleotide sequence of SEQ ID NO: 1.

In accordance with yet another embodiment, the present invention provides an isolated host cell comprising a recombinant expression vector comprising the isolated nucleotide sequence encoding the myonectin (CTRP15) gene.

In another embodiment, the present invention provides a population of cells prepared using the methods described above.

In accordance with an embodiment, the present invention provides an antibody, or antigen binding portion thereof, which specifically binds to a portion of the myonectin CTRP 15 protein.

In accordance with yet another embodiment, the present invention provides a pharmaceutical composition comprising a myonectin (CTRP15) isolated nucleic acid, or a recombinant expression vector comprising the myonectin (CTRP15) isolated nucleic acid, or a myonectin (CTRP15) protein or functional portion thereof, or a myonectin (CTRP15) polypeptide, or a host cell or population of cells comprising the myonectin (CTRP15) isolated nucleic acid, or an antibody to myonectin (CTRP15) protein or antigen binding portion thereof, and a pharmaceutically acceptable carrier.

In accordance with another embodiment, the present invention provides a method of modulating lipid and/or glucose metabolism in a subject, comprising administering to the host a pharmaceutical composition comprising a myonectin (CTRP15) isolated nucleic acid, or a recombinant expression vector comprising the myonectin (CTRP15) isolated nucleic acid, or a myonectin (CTRP15) protein or functional portion thereof, or a myonectin (CTRP15) polypeptide, or a host cell or population of cells comprising the myonectin (CTRP15) isolated nucleic acid, or an antibody to myonectin (CTRP15) protein or antigen binding portion thereof, and a pharmaceutically acceptable carrier.

In accordance with an embodiment, the present invention provides a method of suppressing the expression of autophagy genes in a subject, comprising administering to the host a pharmaceutical composition comprising a myonectin (CTRP15) isolated nucleic acid, or a recombinant expression vector comprising the myonectin (CTRP15) isolated nucleic acid, or a myonectin (CTRP15) protein or functional portion thereof, or a myonectin (CTRP15) polypeptide, or a host cell or population of cells comprising the myonectin (CTRP15) isolated nucleic acid, or an antibody to myonectin (CTRP15) protein or antigen binding portion thereof, and a pharmaceutically acceptable carrier.

In accordance with an embodiment, the present invention provides a method of inhibiting LC3 lipidation and autophagosome-dependent p62 degradation in a subject, comprising administering to the host a pharmaceutical composition comprising a myonectin (CTRP15) isolated nucleic acid, or a recombinant expression vector comprising the myonectin (CTRP15) isolated nucleic acid, or a myonectin (CTRP15) protein or functional portion thereof, or a myonectin (CTRP15) polypeptide, or a host cell or population of cells comprising the myonectin (CTRP15) isolated nucleic acid, or an antibody to myonectin (CTRP15) protein or antigen binding portion thereof, and a pharmaceutically acceptable carrier.

In accordance with an embodiment, the present invention provides a method of activating the Akt/mTOR pathway in a subject, comprising administering to the host a pharmaceutical composition comprising a myonectin (CTRP15) isolated nucleic acid, or a recombinant expression vector comprising the myonectin (CTRP15) isolated nucleic acid, or a myonectin (CTRP15) protein or functional portion thereof, or a myonectin (CTRP15) polypeptide, or a host cell or population of cells comprising the myonectin (CTRP15) isolated nucleic acid, or an antibody to myonectin (CTRP15) protein or antigen binding portion thereof, and a pharmaceutically acceptable carrier.

DETAILED DESCRIPTION OF THE INVENTION

Figure 1:
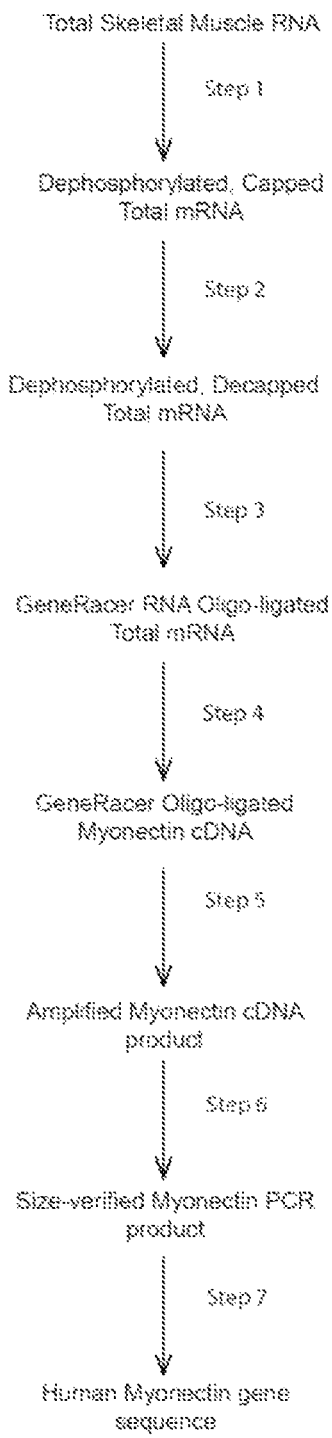
FIG. 1 is a schematic diagram representing the protocol used for cloning human myonectin (CTRP15).

Herein is provided the first characterization of myonectin (CTRP15) protein, with in vitro and in vivo evidence that it is a novel myokine with important metabolic function. Unlike the other CTRPs characterized to date, myonectin (CTRP15) is expressed and secreted predominantly by skeletal muscle. Myonectin (CTRP15) functions as a myokine that mediates crosstalk between skeletal muscle and other metabolic compartments (e.g., adipose tissue and liver) to coordinate the integration of whole-body metabolism. Consistent with this notion, the expression and secretion of myonectin by skeletal muscle is highly responsive to acute nutritional and metabolic changes (e.g., fast/re-fed cycle and exercise), as well as chronic alteration in energy state of the animals (e.g., diet-induced obesity).

The term "nucleic acid" as used herein, includes "polynucleotide," "oligonucleotide," and "nucleic acid molecule," and generally means an isolated or purified polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% or 80%, or can be 100%.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligodeoxyribonucleotide. The appropriate length of a primer depends on the intended use of the primer but typically ranges from about 10 to about 30 nucleotides. Short primer molecules generally require cooler temperatures to form sufficiently stable hybrid complexes with the template. A primer need not reflect the exact sequence of the template but must be sufficiently complementary to specifically hybridize with a template. When primer pairs are referred to herein, the pair is meant to include one forward primer which is capable of hybridizing to the sense strand of a double-stranded target nucleic acid (the "sense primer") and one reverse primer which is capable of hybridizing to the antisense strand of a double-stranded target nucleic acid (the "antisense primer").

"Probe" refers to an oligonucleotide which binds through complementary base pairing to a sub-sequence of a target nucleic acid. A primer may be a probe. It will be understood by one of skill in the art that probes will typically substantially bind target sequences lacking complete complementarity with the probe sequence depending upon the stringency of the hybridization conditions. The probes are typically directly labeled (e.g., with isotopes or fluorescent moieties) or indirectly labeled such as with biotin to which a streptavidin complex may later bind. By assaying for the presence or absence of the probe, one can detect the presence or absence of the target, by Southern blot for example.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2µ plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA or RNA based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, puromycin resistance genes and ampicillin resistance genes. In accordance with an embodiment, the expression vector can be pCR2.1 TOPO vector (Invitrogen), for example.

The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, the tet-on promoter, or the ubiquitin C promoter, for example.

In accordance with an embodiment, the isolated or purified polypeptides, and proteins of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

When the isolated or purified polypeptides and proteins of the invention (including functional portions and functional variants) are in the form of a salt, preferably, the polypeptides are in the form of a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The isolated or purified polypeptides, and/or proteins of the invention (including functional portions and functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2005; *Peptide and Protein Drug*

*Analysis*, ed. Reid, R., Marcel Dekker, Inc., 2000; *Epitope Mapping*, ed. Westwoood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., *Molecular Cloning: A Laboratory Manual*, $3^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 2007. Further, some of the polypeptides, and proteins of the invention (including functional portions and functional variants thereof) can be isolated and/or purified from a source, such as a plant, a bacterium, an insect, a mammal, e.g., a rat, a mouse, a human, etc. Methods of isolation and purification are well-known in the art. Alternatively, the polypeptides, and/or proteins described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive polypeptides, and proteins can be synthetic, recombinant, isolated, and/or purified.

Included in the scope of the invention are conjugates, e.g., bioconjugates, comprising any of the inventive polypeptides, or proteins (including any of the functional portions or variants thereof), nucleic acids, recombinant expression vectors, host cells, populations of host cells, or antibodies, or antigen binding portions thereof. Conjugates, as well as methods of synthesizing conjugates in general, are known in the art (See, for instance, Hudecz, F., *Methods Mol. Biol.* 298: 209-223 (2005) and Kirin et al., *Inorg. Chem.* 44(15): 5405-5415 (2005)).

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell is preferably a eukaryotic cell. More preferably, the host cell is a myocyte and/or pre-adipocyte, for example, a mouse C2C12 myocyte and 3T3-L1 cell. Most preferably, the host cell is a human cell.

Also provided by an embodiment of the invention is a population of cells comprising at least one host cell described herein. The population of cells can be a heterogeneous population comprising the host cell comprising any of the recombinant expression vectors described, in addition to at least one other cell, e.g., a host cell (e.g., a myocyte cell), which does not comprise any of the recombinant expression vectors, or a cell other than a myocyte, e.g., a B cell, a macrophage, a neutrophil, an erythrocyte, a hepatocyte, an endothelial cell, an epithelial cells, a pre-adipocyte cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

The host referred to in the inventive methods can be any host. Preferably, the host is a mammal. As used herein, the term "mammal" refers to any mammal, including, but not limited to, mammals of the order Rodentia, such as mice and hamsters, and mammals of the order Lagomorpha, such as rabbits. It is preferred that the mammals are from the order Carnivora, including Felines (cats) and Canines (dogs). It is more preferred that the mammals are from the order Artiodactyla, including Bovine (cows) and Swine (pigs) or of the order Perssodactyla, including Equine (horses). It is most preferred that the mammals are of the order Primates, Ceboids, or Simoids (monkeys) or of the order Anthropoids (humans and apes). An especially preferred mammal is the human.

Another embodiment of the invention further provides an antibody, or antigen binding portion thereof, which specifically binds to the myonectin (CTRP15) protein or isolated or purified peptide fragments thereof described herein. In one embodiment, the antibody, or antigen binding portion thereof, binds to an epitope or peptide fragment which contains any of the mutant amino acids which differ from the wild-type proteins. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the mutated portion of the myonectin (CTRP15) protein or peptide fragments thereof of the present invention, such that there is minimal cross-reaction with other peptides or proteins.

Methods of testing antibodies for the ability to bind to any functional portion of any of the myonectin (CTRP15) protein or isolated or purified peptide fragments thereof are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Suitable methods of making antibodies are known in the art. For instance, standard hybridoma methods are described in, e.g., Köhler and Milstein, *Eur. J.* Immunol., 5, 511-519 (1976), Harlow and Lane (eds.), *Antibodies: A Laboratory Manual*, CSH Press (1988), and C. A. Janeway et al. (eds.), *Immunobiology*, $5^{th}$ Ed., Garland Publishing, New York, N.Y. (2001)). Alternatively, other methods, such as EBV-hybridoma methods (Haskard and Archer, *J. Immunol. Methods*, 74(2), 361-67 (1984), and Roder et al., *Methods Enzymol.*, 121, 140-67 (1986)), and bacteriophage vector expression systems (see, e.g., Huse et al., *Science*, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Phage display furthermore can be used to generate the antibody of the invention. In this regard, phage libraries encoding antigen-binding variable (V) domains of antibodies can be generated using standard molecular biology and recombinant DNA techniques (see, e.g., Sambrook et al. (eds.), *Molecular Cloning, A Laboratory Manual*, 3rd Edition, Cold Spring Harbor Laboratory Press, New York (2001)). Phages encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., *J. Mol. Biol.*, 235, 959-973 (1994).

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The polypeptides, proteins, (including functional portions and functional variants thereof), nucleic acids, recombinant expression vectors, host cells (including populations thereof), and antibodies (including antigen binding portions thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% or 80%, or can be 100%.

The choice of carrier will be determined in part by the particular myonectin (CTRP15) protein, as well as by the particular method used to administer the myonectin (CTRP15) protein. Accordingly, there are a variety of suitable formulations of the pharmaceutical composition of the invention. The following formulations for parenteral, subcutaneous, intravenous, intramuscular, intraarterial, intrathecal and interperitoneal administration are exemplary and are in no way limiting. More than one route can be used to administer the myonectin (CTRP15) protein, and in certain instances, a particular route can provide a more immediate and more effective response than another route.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the myonectin (CTRP15) protein in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Injectable formulations are in accordance with the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

For purposes of the invention, the amount or dose of the myonectin (CTRP15) protein administered should be sufficient to effect, e.g., a therapeutic or prophylactic response, in the subject over a reasonable time frame. The dose will be determined by the efficacy of the particular myonectin (CTRP15) protein and the condition of a human, as well as the body weight of a human to be treated.

The dose of the myonectin (CTRP15) protein also will be determined by the existence, nature and extent of any adverse side effects that might accompany the administration of a particular myonectin (CTRP15) protein. Typically, the attending physician will decide the dosage of the myonectin (CTRP15) protein with which to treat each individual patient, taking into consideration a variety of factors, such as age, body weight, general health, diet, sex, vaccine protein to be administered, route of administration, and the severity of the condition being treated. By way of example and not intending to limit the invention, the dose of the myonectin (CTRP15) protein can be about 0.001 to about 1000 mg/kg body weight of the subject being treated/day, from about 0.01 to about 10 mg/kg body weight/day, about 0.01 mg to about 1 mg/kg body weight/day. In a preferred embodiment, the dose of the myonectin (CTRP15) protein administered is about 5-10 mg/kg/day.

Alternatively, the myonectin (CTRP15) protein can be modified into a depot form, such that the manner in which the vaccine protein is released into the body to which it is administered is controlled with respect to time and location within the body (see, for example, U.S. Pat. No. 4,450,150). Depot forms of myonectin (CTRP15) proteins can be, for example, an implantable composition comprising the vaccine proteins and a porous or non-porous material, such as a polymer, wherein the myonectin (CTRP15) protein is encapsulated by or diffused throughout the material and/or degradation of the non-porous material. The depot is then implanted into the desired location within the body and the myonectin (CTRP15) proteins are released from the implant at a predetermined rate.

With respect to the inventive method of detecting any of the myonectin (CTRP15) protein or nucleic acid molecules in a host, the sample of cells of the host can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting can take place in vitro or in vivo with respect to the host. Preferably, the contacting is in vitro.

As used herein, the term "treatment," or "modulation" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. The term "treatment," can also mean prolonging survival as compared to expected survival if not receiving treatment. The term "treatment," is an intervention performed with the intention of preventing the development of a disorder or altering the pathology of a disorder. Accordingly, the term "treatment," refers to both therapeutic treatment and prophylactic or preventative measures.

The terms "metabolic disease" and "metabolic disorder" are used in the broadest sense and include any condition that is associated with abnormal fatty acid and/or insulin metabolism, and would benefit from treatment of the present invention. This includes chronic and acute disorders or diseases including those pathological conditions which predispose the mammal to the disorder in question. The terms include, without limitation, disorders associated with hyperlipidemia as well as diabetes and cardiovascular diseases. In one or more preferred embodiments, the disorder to be treated in accordance with the present invention is obesity, type 2 diabetes and cardiac hypertrophy.

In one embodiment a tissue sample is obtained from the musculature or adipose tissue of a mammal. The sample may be obtained by any method known in the art, such as by biopsy or by a surgical procedure. Such methods for obtaining tissue samples are well known in the art. The sample is preferably obtained from a part of the anatomy that is known to comprise stem cells.

In a preferred embodiment, a small tissue sample is obtained from a donor during a surgical procedure. The sample may be, for example, a sample of myocytes. Preferably, the donor is the patient that will receive an autologous transplant of differentiated cells.

In accordance with an embodiment, the present invention provides a method of modulating lipid and/or glucose metabolism in a subject suffering from a metabolic disease comprising (a) obtaining mammalian pluripotent/multipotent stem cells, (b) initiating differentiation of the mammalian pluripotent/multipotent stem cells into a population of differentiated cells comprising the methods described above, (c) transfecting the differentiated cells using a recombinant vector comprising the myonectin (CTRP15) gene, (d) analyzing the development of differentiated cells in culture, and (e) transplanting the differentiated cells into the subject.

For example, following proliferation and differentiation, stem cells are transplanted into a patient. Preferably the patient will receive from about 0.5 million to about 80 million cells, more preferably about 0.5 million to about 10 million cells, and still more preferably 4 million to about 8 million cells.

In accordance with an embodiment, the present invention provides a method of suppressing the expression of autophagy genes in a subject, comprising administering to the host a pharmaceutical composition comprising a myonectin (CTRP15) isolated nucleic acid, or a recombinant expression vector comprising the myonectin (CTRP15) isolated nucleic acid, or a myonectin (CTRP15) protein or functional portion thereof, or a myonectin (CTRP15) polypeptide, or a host cell or population of cells comprising the myonectin (CTRP15) isolated nucleic acid, or an antibody to myonectin (CTRP15) protein or antigen binding portion thereof, and a pharmaceutically acceptable carrier.

In accordance with an embodiment, the present invention provides a method of inhibiting LC3 lipidation and autophagosome-dependent p62 degradation in a subject, comprising administering to the host a pharmaceutical composition comprising a myonectin (CTRP15) isolated nucleic acid, or a recombinant expression vector comprising the myonectin (CTRP15) isolated nucleic acid, or a myonectin (CTRP15) protein or functional portion thereof, or a myonectin (CTRP15) polypeptide, or a host cell or population of cells comprising the myonectin (CTRP15) isolated nucleic acid, or an antibody to myonectin (CTRP15) protein or antigen binding portion thereof, and a pharmaceutically acceptable carrier.

In accordance with an embodiment, the present invention provides a method of activating the Akt/mTOR pathway in a subject, comprising administering to the host a pharmaceutical composition comprising a myonectin (CTRP15) isolated nucleic acid, or a recombinant expression vector comprising the myonectin (CTRP15) isolated nucleic acid, or a myonectin (CTRP15) protein or functional portion thereof, or a myonectin (CTRP15) polypeptide, or a host cell or population of cells comprising the myonectin (CTRP15) isolated nucleic acid, or an antibody to myonectin (CTRP15) protein or antigen binding portion thereof, and a pharmaceutically acceptable carrier.

EXAMPLES

The following examples further illustrate the invention but, of course, should not be construed as in any way limiting its scope.

Antibodies and chemicals. Mouse monoclonal anti-FLAG M2 antibody was obtained from Sigma and rat monoclonal anti-HA (clone 3F10) antibody was obtained from Roche Applied Science. AICAR (an AMPK activator) was obtained from Calbiochem (city state); insulin, isoproteronol, ionomycin, and epinephrine from Sigma (St. Louis, Mo.); forskolin from Cell Signaling Technology. Rabbit monoclonal antibodies recognizing p62, ULK1, phosphor-ULK1 (Ser-757), Akt, phosphor-Akt (Thr-308), p70 S6 Kinase, phosphor-p70 S6 kinase (Thr-389), and β-Tubulin were obtained from Cell Signaling Technology. Rabbit polyclonal antibody recognizing LC3B was obtained from Sigma-Aldrich. FRAP/mTOR inhibitor was obtained from Cell Signaling Technology.

Animals. Eight-week-old male or female wild-type C57BL/6 mice were purchased from the Jackson Laboratory and were housed in polycarbonate cages on a 12-hour light-dark photocycle, with free access to water and standard laboratory chow diet (no. 5001, Lab Diet, PMI Nutrition International, St. Louis, Mo.) throughout the study period. Separate cohorts of mice were fed a high-fat diet (60% kcal derived from fat; D12492) or an isocaloric-matched low-fat diet (10% kcal derived from fat; D12450B) purchased from Research Diets Inc. (New Brunswick, N.J.). HF diet was provided for a period of 12-14 weeks, starting at 4-5 weeks of age, to make mice diet-induced obese (DIO). Blood samples were collected for serum analysis. Tissues were collected, snap-frozen in liquid nitrogen, and kept at −80° C.

Animals were fasted for 24 h and injected via tail vein with either 10 μL/g body weight of 20% glucose solution, Hepes buffer (vehicle control), or 1 μg/g body weight recombinant myonectin protein. Serum and tissues were harvested 4 h post-injection. All animal protocols were approved by the Institutional Animal Care and Use Committee of Johns Hopkins University School of Medicine.

Cloning of mouse myonectin. A search for CTRP-like proteins in the NCBI GenBank databases identified a novel cDNA encoding a previously undescribed member of the CTRP family, which we designated as CTRP15/myonectin. Based on genomic DNA and EST sequences, a PCR approach was used to clone the entire coding region of mouse myonectin from a skeletal muscle cDNA library (Clontech). For mouse myonectin, the primer pair used was 5'-CAGCATG-GCCTCGACCCGCCGCCCGTCGGA G-3' (SEQ ID NO: 3) and 5'-CAGCTGCTGCAGGCTCTTACCCTT A-3' (SEQ ID NO: 4). The PCR product was agarose gel-purified and cloned into the pCR2.1 TOPO vector (Invitrogen). The entire cDNA insert was sequenced.

cDNA constructs. C-terminal FLAG epitope (DYKD-DDDK (SEQ ID NO: 5)-tagged mouse myonectin cDNA was generated by PCR, cloned into the mammalian expression vector (pCDNA3.1; Invitrogen), and verified by DNA sequencing. C-terminal HA epitope (YPYDVPDYA (SEQ ID NO: 6))-tagged mouse adiponectin and all CTRPs used in this study were generated as previously described (*Proc. Natl. Acad. Sci. USA*, (2004) 101: 10302-10307; *FASEB J.* (2009) 23: 241-258; *Biochem. J.* (2008) 416: 161-177; and *J. Biol. Chem.* (2011), 286: 15652-15665).

Generation of myonectin-specific antibody. Rabbit polyclonal anti-peptide antibody that can specifically recognize mouse myonectin (epitope 77-KQSDKGI NSKRRSKARR-93 (SEQ ID NO: 7) was generated (YenZym Antibodies, LLC) and tested against conditioned medium harvested from myonectin-transfected HEK 293T cells.

Protein purification. Recombinant full-length mouse myonectin, containing a C-terminal FLAG-tagged epitope, was produced in mammalian cells as described previously (*Biochem. J.* (2008), supra). The presence of carbohydrate moiety and the formation of higher order oligomers necessitate that recombinant myonectin be produced in mammalian cells to ensure biologically active protein. Briefly, HEK 293 cells (Grip-Tite™ cells, Invitrogen) were cultured in DMEM containing 10% (v/v) bovine calf serum supplemented with antibiotics. Transfections were performed in HEK 293 cells using the calcium phosphate method (*Cell* (1977) 11: 223-232). At 48 hours post-transfection, medium was replaced with serum-free Opti-MEM (Invitrogen) supplemented with vitamin C (0.1 mg/ml). Supernatants were collected three times, every 48 hours, pooled, and purified using an anti-FLAG affinity gel according to the manufacturer's protocol (Sigma), then eluted with 150 μg/ml FLAG peptide (Sigma). Purified proteins were dialyzed against 20 mM Hepes buffer (pH 8.0) containing 135 mM NaCl in a 10 kDa cut-off Slide-A-Lyzer dialysis cassette (Pierce, Rockford, Ill.). Protein concentration was determined using a Coomassie Plus protein assay reagent (Thermo Scientific), and samples were stored at −80° C.

Cloning of human myonectin (CTRP15). A schematic of the cloning protocol is provided in FIG. 1. Commercially purchased human total skeletal muscle RNA (Applied Biosystems, Ambion product # AM7982) is incubated in Calf Intestinal Phosphatase (10 U/μl) and CIP buffer (0.5 mM Tris-HCl, pH 8.5 and 1 mM EDTA) for 1 hour at 50° C., followed by a standard phenol-chloroform RNA extraction. This reaction will yield isolated, decapped total skeletal muscle mRNA.

The decapped total skeletal muscle mRNA is added to Tobacco Acid Pyrophosphatase (0.5 U/μl) in TAP buffer (0.5M sodium acetate, pH 6.0; 10 mM EDTA; 1% β-mercaptoethanol and 0.1% Triton X-100) and incubated for 37° C. for 1 hour. This step is followed by a standard phenol-chloroform RNA extraction, yielding decapped, dephosphorylated total skeletal muscle mRNA.

The decapped, dephosphorylated total skeletal muscle mRNA is added to GeneRacer RNA Oligo (25 μg) and incubated for 65° C. for 5 minutes to relax the mRNA structure. The reaction is then briefly chilled on ice then added to a ligation mixture: 10 mM ATP, T4 RNA Ligase (5 U/μl), 330 mM Tris-acetate (pH 7.8), 660 mM potassium acetate, 100 mM magnesium acetate and 5 mM DTT. This step is followed by a standard phenol-chloroform RNA extraction, yielding GeneRacer Oligo-ligated total skeletal muscle mRNA.

Figure 2:
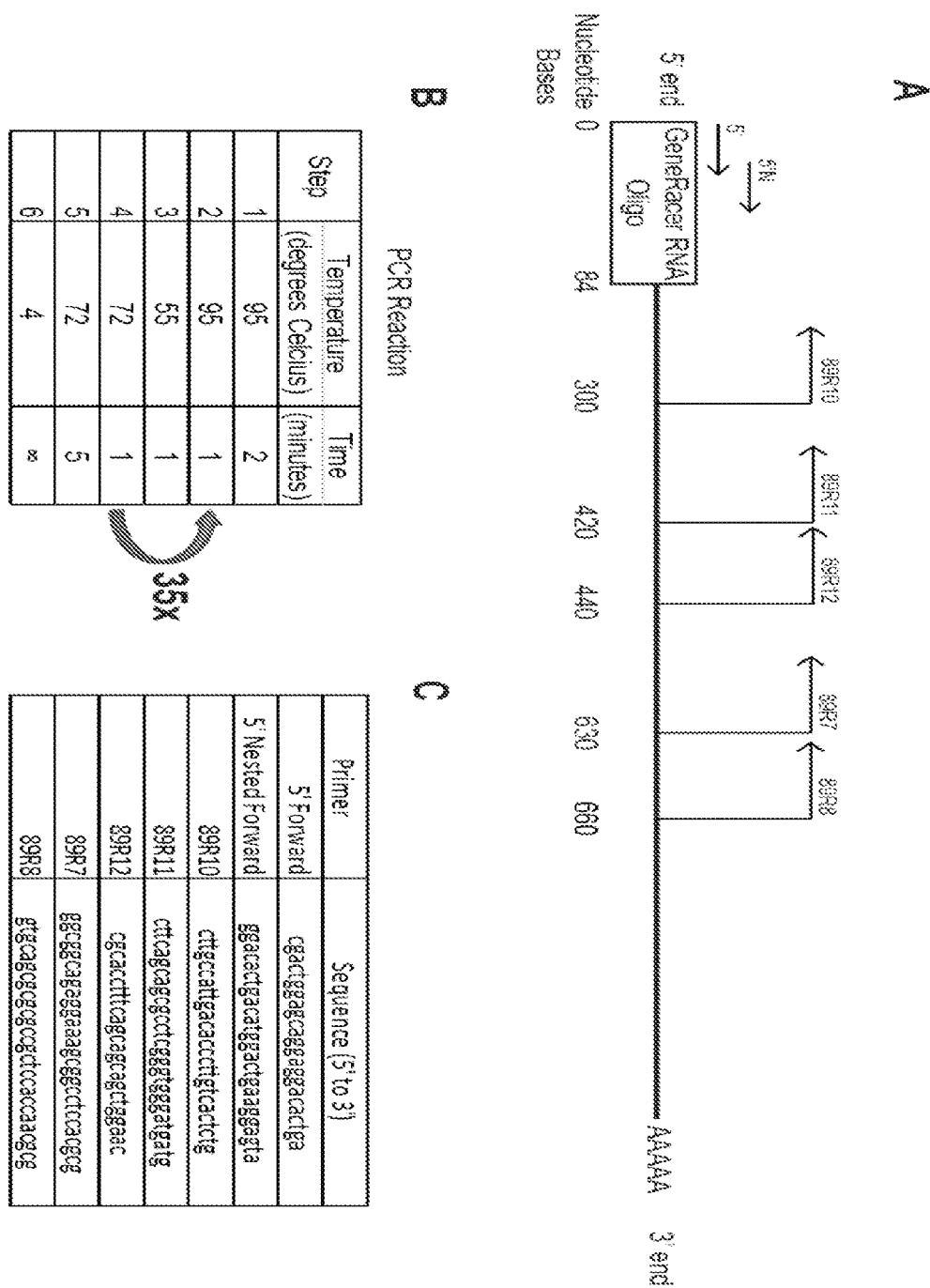
FIG. 2 provides the experimental scheme for cloning human myonectin. (A) A schematic diagram representing the myonectin mRNA sequence with predicted primer landing sites. Arrows indicate direction of primer. (B) A summary of PCR reaction protocol used. (C) A set of PCR primer sequences (SEQ ID NOS: 26-32) for corresponding human gene targets.

Reverse transcription of ligated mRNA using myonectin-specific primers. This step utilizes SuperScript III Reverse Transcriptase Module (Invitrogen, product #45-0167) in combination with predesigned myonectin-specific primers (sequences listed below). Product from step 3 is added to a mixture of dNTP's (in 1 mM Tris HCl, pH 7.5), 5' forward GeneRacer and myonectin-specific primer 89R8. Given the primers used, this reaction should yield a cDNA product which is specific to the 5' end of the human myonectin. The reaction mixture is incubated at 65° C. for 5 minutes to relax the mRNA structure then briefly chilled on ice. Next, the following components are added to the reaction: 0.1M DTT, SuperScript III Reverse Transcriptase (200 U/μl), 50 mM mM Tris-HCl (pH 7.5), 75 mM potassium chloride and 3 mM magnesium chloride. The reaction is incubated at 55° C. for 45 minutes to reverse transcribe the mRNA, then the enzymatic activity is deactived at 70° C. for 15 minutes. RNase H (2 U/reaction) is then added and reaction incubated at 37° C. for 20 minutes to remove remaining mRNA. This step yields a cDNA sequence for the myonectin, with the GeneRacer Oligo sequence at the beginning and ending at 660 base pairs (FIG. 2A), where the verified 89R8 primer site lies. The next steps are used to amplify and validate the myonectin cDNA.

The cDNA product is added to a mixture containing 5' Forward primers (10 μM), 89R8 primers (10 μM) and Platinum PCR Supermix (Invitrogen product #11306-016). This reaction is cycled using the PCR reaction (FIG. 2B) and should yield enough cDNA for further analysis.

Recombinant protein injection. Experiments were carried out as previously described (*Biochem. J.* (2008), supra, *J. Biol. Chem.*, (2010) 285: 39691-39701). Briefly, food was removed in the morning (around 8-9 am), 2 hours prior to recombinant protein injection; drinking water was supplied for the duration of the experiment. Recombinant myonectin (5 µg/g body weight) or the equivalent volume of vehicle buffer [20 mM Hepes (pH 8.0) containing 135 mM NaCl] was injected intraperitoneally into 10-week-old C57BL/6 mice (n=6). Serum samples were harvested by tail bleeding at baseline (time 0) and every hour for 5 hours post injection, and separated using Microvette® CB 300 (Sarstedt). Glucose concentrations were also measured using a glucometer (BD Pharmingen) when tail blood was collected at the indicated time points.

Isolation of skeletal muscle and liver. Mice were sacrificed and soleus and plantaris muscles and livers were immediately isolated and snap-frozen in liquid nitrogen. Homogenized muscle cell lysates were prepared in lysis buffer (TPER, Thermo Scientific) containing protease and phosphatase inhibitor cocktails (Sigma). Protein content was quantified using Coomasie Plus protein reagent (Thermo Scientific).

Cell Culture—

Mouse C2C12 myocytes and mouse 3T3-L1 pre-adipocytes and rat H4IIE hepatocytes were cultured and differentiated into myotubes adipocytes, and liver respectively, as previously described (*J. Biol. Chem.*, (2011), supra, *J. Biol. Chem.*, (2010), supra). Differentiated cells were stimulated with insulin (100 nM), AICAR (1 mM), or forskolin (1 µM) for the indicated time and total RNAs were isolated and subjected to quantitative real-time PCR analysis for myonectin expression. To induce autophagy, cells were placed in autophagy media: Dulbecco's Modified Eagle Medium (DMEM) containing 0.1% BSA (Sigma), but lacking glucose, L-glutamine, and sodium pyruvate, for 5 or 24 h. For each experiment, autophagy induction was verified by comparing samples to control cells incubated with DMEM containing 10% FBS (Invitrogen). In all cell culture treatments, 5 mg/mL of recombinant myonectin protein was used.

Fatty Acid uptake assay. Cells were washed twice in PBS and placed in stimulation media (0.5% BSA for 3T3-L1 adipocytes and 0.1% BSA for H4IIE hepatocytes in high glucose, fatty acid-free DMEM at 37° C. and 5% $CO_2$ in an incubator for 2 hours. Next, media was changed to the same DMEM (with 0.5% and 0.1%, respectively, fatty acid-free BSA) containing vehicle control, recombinant myonectin (5 µg/ml), or insulin (50 nM) overnight. Cells were transferred to a 37° C. water bath where 1 µCi/well (in a 24-well format) of [$^3$H]-labelled palmitate (dissolved previously for 1 hour in the fatty-acid-free BSA DMEM) was added for 0, 30, or 60 seconds. Media was then aspirated out and cells were washed twice in cold PBS. Cells were lysed in 10% SDS and transferred to a scintillation vial. Radioactive counts were measured and normalized to protein concentration of final cell lysate.

Palmitate and glucose treatment. Differentiated mouse C2C12 myotubes were washed twice with PBS, followed by addition of 0.1% fatty acid-free BSA (Sigma) in serum- and glucose-free DMEM for 2 hours. Next, the same solution was added with or without 25 mM glucose or 1 µM palmitic acid. The palmitic acid and fatty acid-free BSA mixture was made 1 hr prior to addition to cells and kept at 37° C. to completely dissolve into solution. Total RNA was harvested from cells treated for 18 hours.

Running wheel-induced exercise. C57BL/6 male mice were placed in a cage with or without a running wheel for a period of 2 weeks. They were given ad libitum food access. At the end of the two-week period, mice were fasted overnight (12 hours) and serum and skeletal muscle were harvested for analysis.

Serum and blood chemistry analysis. Mouse serum samples were harvested by tail-bleed and separated using Microvette® CB 300 (Sarstedt). Glucose concentration was determined at time of collection with a glucometer (BD biosciences). Serum triglycerides (Thermofisher), NEFA (Wako), and insulin (Millipore) were determined using commercially available kits.

Quantitative real time PCR analysis. The tissue expression profile of myonectin was determined using mouse tissue cDNA panels (Clontech). Otherwise, total RNAs were isolated from tissues or cell lines using Trizol® and reverse transcribed using Superscript II RNase H-reverse Transcriptase (Invitrogen). Myonectin-specific primers used were 5'-TGCTTGGATGCTGTTCGTCAA-3' (SEQ ID NO: 8) and 5'-CAGATGGGATAAAGGGGCCTG-3' (SEQ ID NO: 9). Quantitative real-time PCR analyses were performed on an Applied Biosystems Prism 7500 Sequence Detection System. Samples were analyzed in 25-µL reactions according to the standard protocol provided in the SyBR® Green PCR Master Mix (Applied Biosystems). Myonectin expression was normalized to 18 S rRNA in each sample. Primer sequences are listed in Supplemental Table S1. Data were normalized to β-Actin and expressed as relative mRNA levels using the ΔΔCt method (Nat Protoc 3, 1101-1108 (2008)).

TABLE 1

Quantitative PCR Primers used

| Name | Forward primer 5'->3' | Reverse primer 5'->3' |
|---|---|---|
| Mouse β-Actin | GGCACCACACCTTCTACAATG (SEQ ID NO: 10) | GGGGTGTTGAAGGTCTCAAAC (SEQ ID NO: 11) |
| Rat β-Actin | ATCTGGCACCACACCTTC (SEQ ID NO: 12) | AGCCAGGTCCAGACGCA (SEQ ID NO: 13) |
| Mouse Atg5 | TGTGCTTCGAGATGTGTGGTT (SEQ ID NO: 14) | ACCAACGTCAAATAGCTGACTC (SEQ ID NO: 15) |
| Rat Atg5 | CCCTCCAGAAGAAAATGGAT (SEQ ID NO: 16) | ATAGCTCAGATGCTCGCTCA (SEQ ID NO: 17) |
| Mouse Atg7 | CCTGCACAACACCAACAC (SEQ ID NO: 18) | CACCTGACTTTATGGCTTCCC (SEQ ID NO: 19) |
| Rat Atg7 | TGTCAGCCTGGCATTTGATAA (SEQ ID NO: 20) | TCACTCATGTCCCAGATCTCA (SEQ ID NO: 21) |
| Mouse Atg12 | TGGCCTCGGAACAGTTGTTTA (SEQ ID NO: 22) | GGGCAAAGGACTGATTCACAT (SEQ ID NO: 23) |
| Rat Atg12 | TTCGGTTGCAGTTTCGCC (SEQ ID NO: 24) | CCATGCCTGTGATTTGCAGTA (SEQ ID NO: 25) |

Immunoblot Analysis. Serum samples were diluted 1:20 in SDS loading buffer [50 mM Tris-HCl, pH 7.4, 2% SDS w/v, 6% glycerol w/v, 1% 2-mercaptoethanol v/v, and 0.01% bromophenol blue w/v] and were separated on 10% Bis-Tris NuPAGE gel (Invitrogen). Each well was loaded with an equivalent of 1 µl serum. For skeletal muscle lysates, 10 µg of protein were loaded and separated on a 10% Bis-Tris NuPAGE gel. Fractionated proteins were then transferred to Protran BA8 nitrocellulose membranes (Whatman), blocked in 2% non-fat milk for 1 hour, and probed with primary antibodies in the presence of 2% non-fat milk overnight Immunoblots were washed 3× (10 minutes each) in PBS containing 0.1% Tween-20 and incubated with horseradish perioxidase-conjugated secondary antibody (Amersham Biosciences) (1:5000) for 1 hour. Blots were washed 3× (10 minutes each) in PBS containing 0.1% Tween 20, developed in ECL reagent (Millipore) for 2-5 minutes, and visualized with MultiImage III FluorChem® Q (Alpha Innotech). Quantifications of signal intensity were performed using Alphaview Software (Alpha Innotech).

Native gel electrophoresis. Non-denaturing, non-reducing gel electrophoresis was carried out as previously described (*PLoS One*, 5: e12765).

Adipose tissue lipolysis. Experiments were performed as previously described (28). Food was removed from mice 2 hours prior to the isolation of epididymal fat pads. Fat pads were cut into 20 mg sections and placed in 500 µl (per piece) of DMEM (high glucose) containing 0.5% fatty acid-free BSA, with or without 1 µM isoproterenol, or purified myonectin (5 µg/ml). Tissue samples in media were kept in a 24-well cell culture dish at 37° C. and 5% $CO_2$. Media were collected at various time points and NEFA content was measured using an absorption-based HR series NEFA kit (Wako Diagnostics).

Autophagy assay. Protocol was adapted from Ogier-Denis et al. (1996) to assess the autophagic degradation of long-lived proteins (*J Biol Chem* 271, 28593-28600). Briefly, H4IIE hepatocytes in 12-well plates (~80% confluence) were incubated for 18 h in complete media (DMEM containing 5 mM glucose, Penicillin/Streptomycin, and 10% FBS) supplemented with 0.2 µCi/mL of L-$^{14}$C-Valine (Moravek Biochemicals, Brea, Calif.). Cells were then washed 3 times in PBS and placed in DMEM (lacking glucose, L-glutamine, and sodium pyruvate but containing 0.1% BSA and 0.5 mM cold valine) supplemented with either 10% FBS, vehicle (Hepes buffer), 5 µg/mL myonectin, or myonectin plus 10 ng/mL FRAP/mTOR inhibitor. Short-lived proteins were degraded within 1 h of incubation, at which time medium was removed and replaced with the same type of fresh medium. Cells were then incubated for an additional 4 h, after which medium was collected. Cells were washed 3× with PBS, scraped, and collected in PBS. A matched volume containing 10% trichloroacetic acid and 1% phosphotungstic acid was added to cells, which were then centrifuged at 4° C. at 600×g for 10 min. Cell medium and the acid-soluble fraction of cell lysate were combined and placed in a scintillation vial containing 2 mL of Soluene 350. The acid-insoluble fraction of the cell lysate was re-suspended in PBS and placed in a separate scintillation vial containing 2 mL of Soluene 350. Percent protein degradation was calculated by dividing counts in the medium plus the acid-soluble fraction of cell lysate with counts in the acid-insoluble fraction of the cell lysate.

Statistical analysis. Comparisons were performed using two-tailed Student's t-tests. Values were considered to be significant at $p<0.05$. For all data *=$p<0.05$; =$p<0.01$; and *=$p<0.001$.

Example 1

Figure 3:
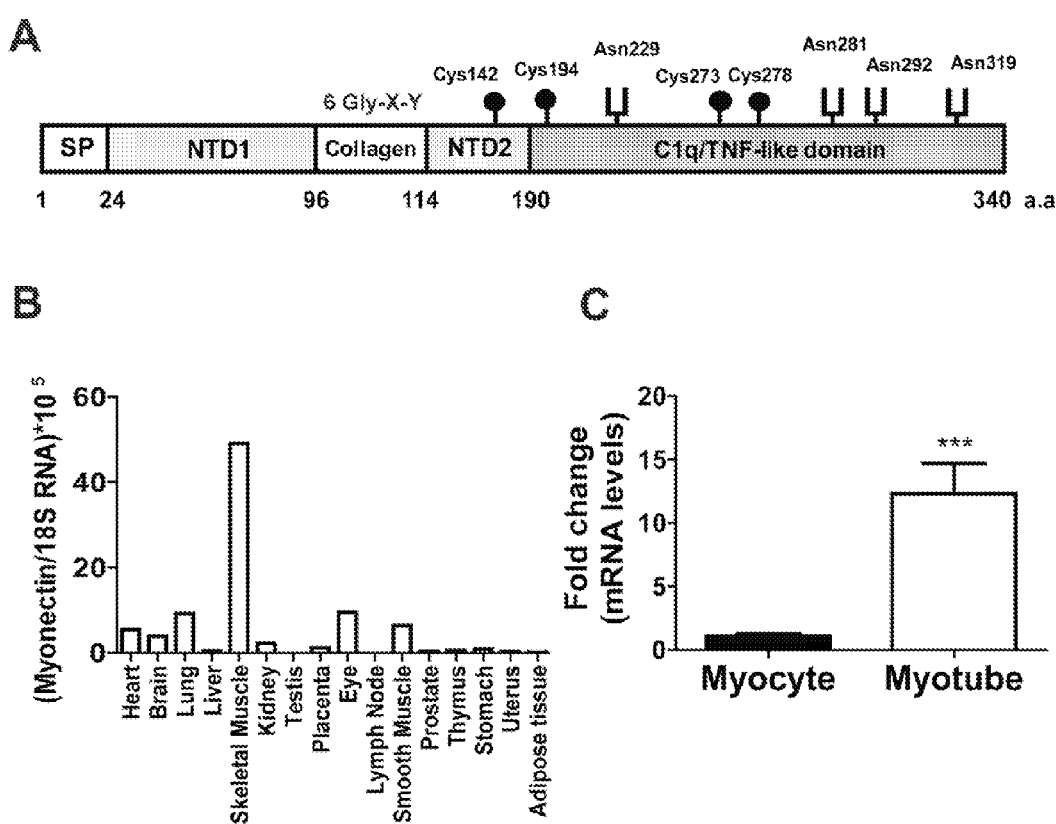
FIG. 3 depicts the deduced myonectin (CTRP15) protein and its expression in skeletal muscle and cultured myotubes. (A), the deduced domain structure of the mouse myonectin (CTRP15) protein of SEQ ID NO: 2. SP, signal peptide; NTD1, N-terminal domain-1; NTD2, N-terminal domain-2. (B) Expression profile of myonectin in mouse tissues. (C), Expression of myonectin transcript in un-differentiated mouse C2C12 myocytes and differentiated myotubes. All quantitative real-time PCR data were normalized to 18S rRNA.

Identification of myonectin (CTRP15) protein. A previously undescribed member of the CTRP family from mouse skeletal muscle was cloned on the basis of sequence homology shared between their C1q domains (FIG. 3A). This novel cDNA (SEQ ID NO: 1) and its encoded protein was designated myonectin (CTRP15). The deduced mouse myonectin protein (SEQ ID NO: 2) consists of five domains: a signal peptide for secretion, an N-terminal domain-1 (NTD1), a short collagen domain with 6 Gly-X-Y repeats, an N-terminal domain-2 (NTD2), and a C-terminal C1q/TNF-like domain. This protein consists of 340 amino acids and contains four Cys residues and four potential N-linked glycosylation sites that conform to the consensus sequence N-X-(Ser/Thr) (*J. Biol. Chem.*, (2005) 280: 3121-3124). The 7.8 kb mouse myonectin gene is located on chromosome 1 (contig NC_000002.11) and contains 8 exons.

Example 2

Expression of myonectin (CTRP15) protein in myotubes and skeletal muscle. In mice, myonectin transcript was predominantly expressed by skeletal muscle, with significantly lower expression in other tissues (FIG. 3B). Consistent with preferential skeletal muscle expression, myonectin was greatly induced in differentiated mouse C2C12 myotubes compared to undifferentiated myoblasts (FIG. 3C), suggesting that myonectin is produced by skeletal muscle fiber and not satellite cells. These data indicate that myonectin is a novel myokine.

Example 3

Figure 4:
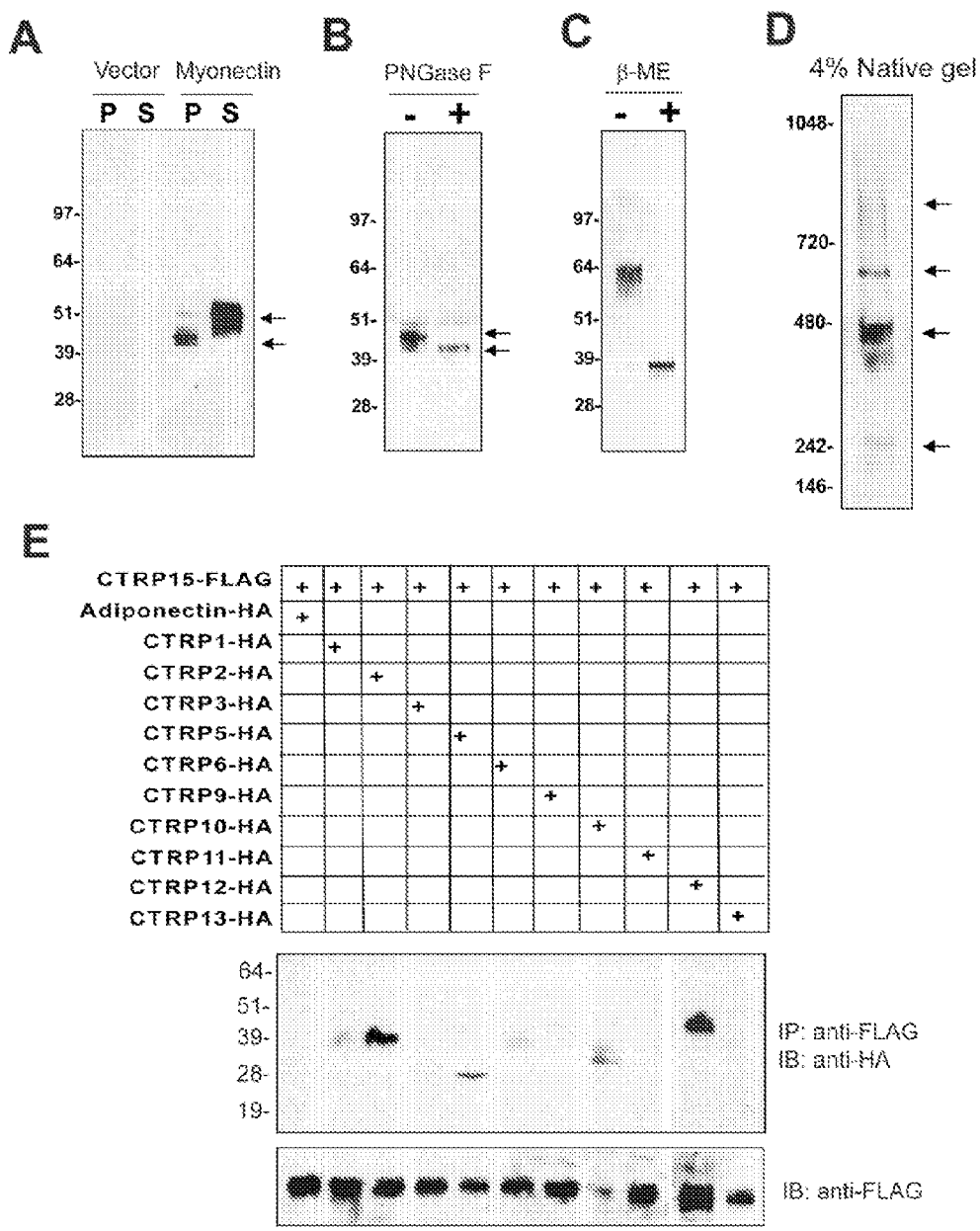
FIG. 4 shows myonectin (CTRP15) is secreted as a multimeric protein that can form heteromeric complexes with other CTRP family members. (A) Immunoblot analysis of cell pellet (P) or supernatant (S) from transfected HEK 293T cells expressing pCDNA3.1 control vector or FLAG epitope-tagged myonectin. (B, C) Immunoblot analysis of myonectin subjected to PNGaseF (B) or β-mercaptoethanol (C) treatment. (D) Native gel immunoblot analysis of myonectin. (E) Immunoprecipitation (IP) followed by immnoblot (IB) analysis of supernatants from HEK 293T cells expressing a combination of FLAG-tagged myonectin and HA-tagged adiponectin or CTRPs.

Myonectin (CTRP15) protein forms disulfide-linked oligomers and heteromeric complexes with other CTRPs. Consistent with the presence of a signal peptide, myonectin was robustly secreted into the conditioned medium when expressed in vitro (FIG. 4A). Secreted myonectin contains N-linked glycans; treatment with PNGase F (an N-glycosidase) reduced the apparent molecular weight of myonectin on immunoblot (FIG. 4B), confirming that one or more of the conserved Asn residues are glycosylated. In the absence of reducing agent (β-ME), myonectin migrated as a dimer on immunoblot (FIG. 4C), indicating the presence of intermolecular disulfide bond. On a non-reducing, non-denaturing, native gel immunoblot, myonectin existed as a multimeric complex, revealing its higher-order oligomeric structure (FIG. 4D). Formation of oligomers is a biochemical feature shared by all CTRPs and proteins of the C1q family. Further, heteromeric complex formation between different CTRPs has been previously demonstrated, suggesting a potential mechanism to generate an expanded repertoire of functionally distinct complexes. Similarly, when co-expressed in mammalian cells (HEK 293T), myonectin formed heteromeric complexes with CTRP2 and CTRP12, and, to a lesser extent, with CTRP5 and CTRP10 (FIG. 4E).

Example 4

Figure 5:
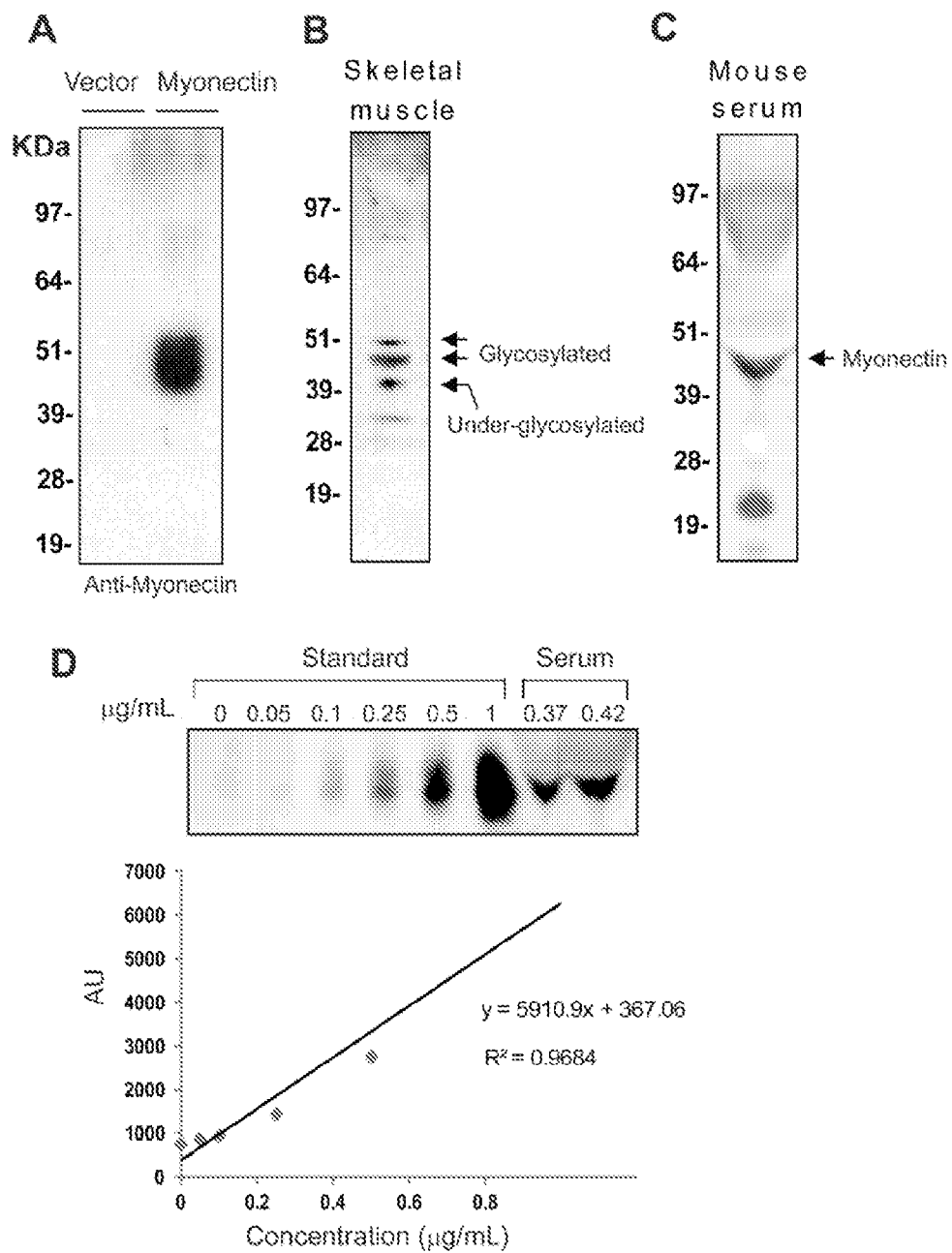
FIG. 5 shows that myonectin (CTRP15) is produced by skeletal muscle and circulates in plasma. (A) Immunoblot analysis of supernatant from HEK 293T cells expressing control vector or FLAG-tagged myonectin using a rabbit anti-myonectin antibody. (B) Immunoblot detection of myonectin in mouse skeletal muscle lysate. Arrows indicate possible isoforms of myonectin resulting from differential glycosylation. (C) Immunoblot detection of myonectin in mouse serum. (D) Estimation of serum concentration of myonectin in wild-type 12-week-old C57BL/6 male mice. Purified recombinant myonectin was used to construct a standard curve.

Myonectin (CTRP15) protein circulates in blood. To examine the endogenous expression of myonectin and to address whether myonectin is a plasma protein and hence may function as an endocrine factor, we generated an anti-peptide antibody that can specifically recognize mouse myonectin secreted from the conditioned medium of transfected cells (FIG. 5A). In mouse skeletal muscle lysate, endogenous myonectin was detected in multiple isoforms, with apparent molecular weights between 40-50 kDa on immunoblot (FIG. 5B), likely reflecting different degrees of glycosylation (FIG. 4A, 4B) due to the presence of multiple conserved Asn residues (FIG. 3A). Western blot analysis of mouse serum revealed the presence of myonectin (FIG. 5C), confirming that it is a secreted protein that circulates in blood. Using purified recombinant myonectin as a standard, serum concentration of myonectin in ad libitum wild-type 12-week-old male mice was determined to be approximately 0.4 µg/ml (FIG. 5D).

Example 5

Figure 6:
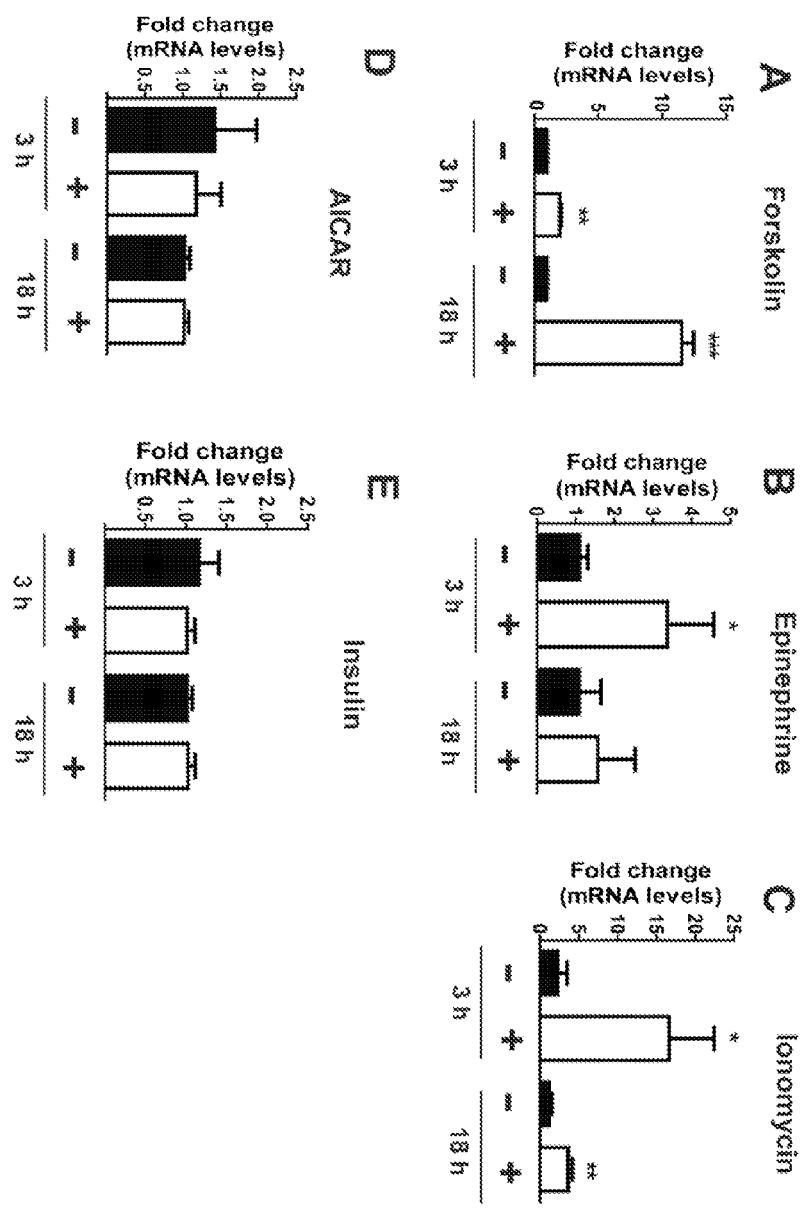
FIG. 6 shows myonectin (CTRP15) expression in myotubes is upregulated by an increase in cellular cAMP or calcium levels. (A-E) Quantitative real-time PCR analysis of myonectin expression mouse C2C12 myotubes treated with vehicle control or 1 μM forskolin, Fsk (A); 1 μM epinephrine, Epi (B); 1 μM ionomycin, Iono (C); 1 mM AICAR (D); or 100 nM insulin, Ins (E). n=8 for each experiment. All expression data were normalized to 18S rRNA and expressed as fold change (normalized to control). All data presented as mean±SEM.

Regulation of myonectin (CTRP15) protein expression in myotubes. Expression of myonectin under different cellular conditions was examined to address whether factors that are known to regulate skeletal muscle physiology also affect myonectin expression. Raising intracellular levels of cAMP (by forskolin and epinephrine) or calcium (by ionomycin) substantially induced expression of myonectin transcript in mouse C2C12 myotubes (FIG. 6A-6C). In contrast, insulin and AICAR (an AMPK activator) had no effect on myonectin expression in myotubes (FIG. 6D, 6E).

Example 6

Figure 7:
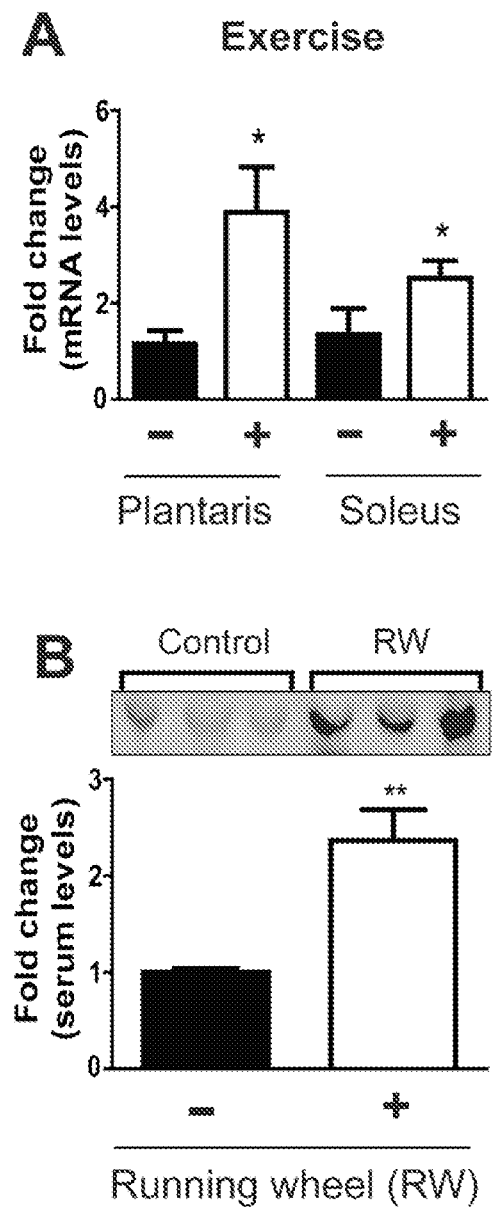
FIG. 7 depicts evidence that exercise increases myonectin (CTRP15) expression in skeletal muscle as well as circulating levels. (A) Quantitative real-time PCR analysis of myonectin expression in plantaris and soleus muscle from mice given access to a running wheel (RW) for two weeks or matched controls with access to locked wheel. All expression data were normalized to 18S rRNA. (B) Immunoblot analysis of serum myonectin from the same cohort of mice. All data are expressed as fold change (normalized to control) and shown as mean±SEM (n=6 mice/group).

Exercise increases myonectin (CTRP15) mRNA expression and circulating levels. The in vitro results of myonectin expression in myotubes suggest that exercise-induced rises in intracellular calcium levels may also upregulate myonectin expression in intact skeletal muscle. Indeed, myonectin expression was significantly induced in soleus (a predominantly slow-twitch muscle fiber) and plantaris (a predominantly fast-twitch muscle fiber) of mice given access to a running wheel for 2 weeks (FIG. 7A). Consistent with enhanced mRNA expression in skeletal muscle of mice subjected to voluntary exercise, circulating levels of myonectin also increased (FIG. 7B), suggesting a potential role of myonectin in exercise-induced physiology.

Example 7

Figure 8:
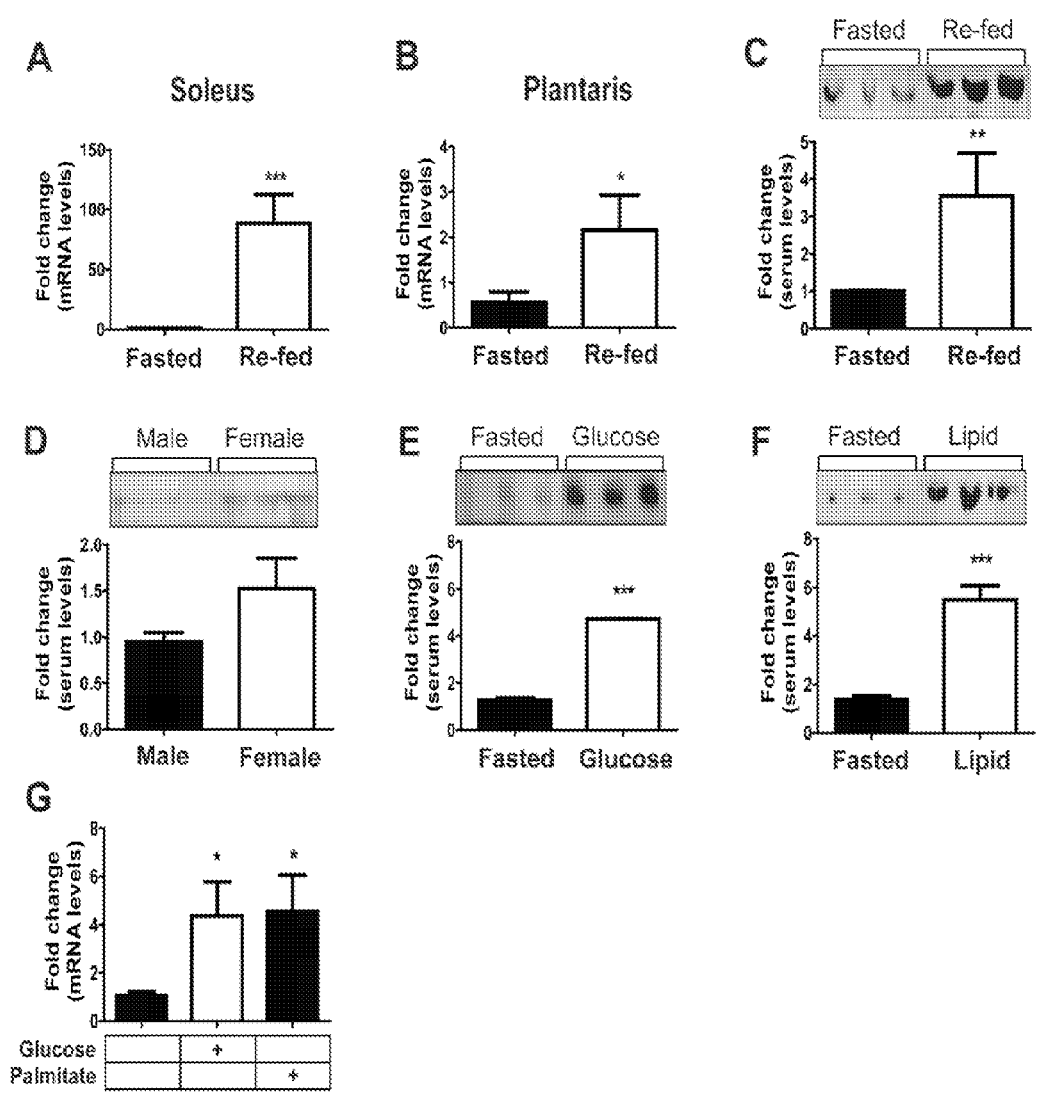
FIG. 8 shows that the nutritional state regulates the expression and circulating levels of myonectin (CTRP15). (A-C) Quantitative PCR analysis of myonectin expression in soleus (A) and plantaris muscle (B), as well as immunoblot quantification of serum levels (C) after a 12-hr fast (Fasted) or fasted followed by 2 hours of unrestricted food access (Re-fed) (n=10 mice/group). All PCR data were normalized to 18S rRNA. (D) Immunoblot quantification of serum myonectin levels in male and female mice subjected to a 12-hour fast (n=10 mice/group). (E-F) Immunoblot quantification of serum myonectin levels in mice subjected to a 12-hour fast (Fasted) or fasted and gavaged with 10 μl/g body weight of either 10% glucose (E) or corn oil (F) (n=10 mice/group). (G) Quantitative PCR analysis of myonectin expression in C2C12 myotubes cultured in serum-free media containing no glucose/lipids (control) or 25 mM glucose or 1 μM palmitate for 18 hours (n=8/group). All data are expressed as fold change (normalized to control) and shown as mean±SEM.

Metabolic state regulates myonectin (CTRP15) protein expression and circulating levels. Given that exercise induces myonectin expression in skeletal muscle, the issue of whether short- and long-term changes in nutritional/metabolic state also regulate myonectin expression and circulating levels was investigated. Surprisingly, an overnight fast greatly suppressed myonectin expression, but a 2-hour refeeding period (following an overnight fast) dramatically upregulated its mRNA expression in skeletal muscle (FIG. 8A, 8B). Intriguingly, refeeding induced myonectin mRNA expression to a much greater extent in soleus than in plantaris muscle fiber of both male and female mice (data not shown). Consistent with the mRNA data, fasting reduced, but refeeding substantially increased, circulating levels of myonectin (FIG. 8C). Interestingly, fasted females also tended to have higher circulating levels of myonectin compared to male mice (FIG. 8D), a trend which persisted upon refeeding (data not shown).

In a separate cohort of mice, it was determined whether the carbohydrate or lipid component within the diet was responsible for the induction of myonectin expression and secretion in the fasted/re-fed state. Overnight fasted male mice were gavaged with a bolus of glucose or lipid (corn oil). Sera were collected from these animals 2 hours post gavage and subjected to Western blot analysis. Both glucose and lipid were equally potent at increasing circulating levels of myonectin in the re-fed state (FIG. 8E, 8F). These data raised the possibility that the presence of nutrient (carbohydrate or lipid) in the gastrointestinal tract induced the secretion of a gut-derived hormone (e.g., incretins such as GLP-1 and GIP) that, in turn, upregulated myonectin expression and secretion from the skeletal muscle. To rule out this possibility, differentiated C2C12 myotubes cultured in serum-free media were starved of glucose and lipid, and then stimulated with glucose or free fatty acid (palmitate). In the absence of any potential gut-derived hormones, both glucose and free fatty acid were able to acutely upregulate myonectin expression in vitro (FIG. 8G). These data suggest that nutrient flux through muscle cells may directly regulate myonectin expression.

Example 8

Figure 9:
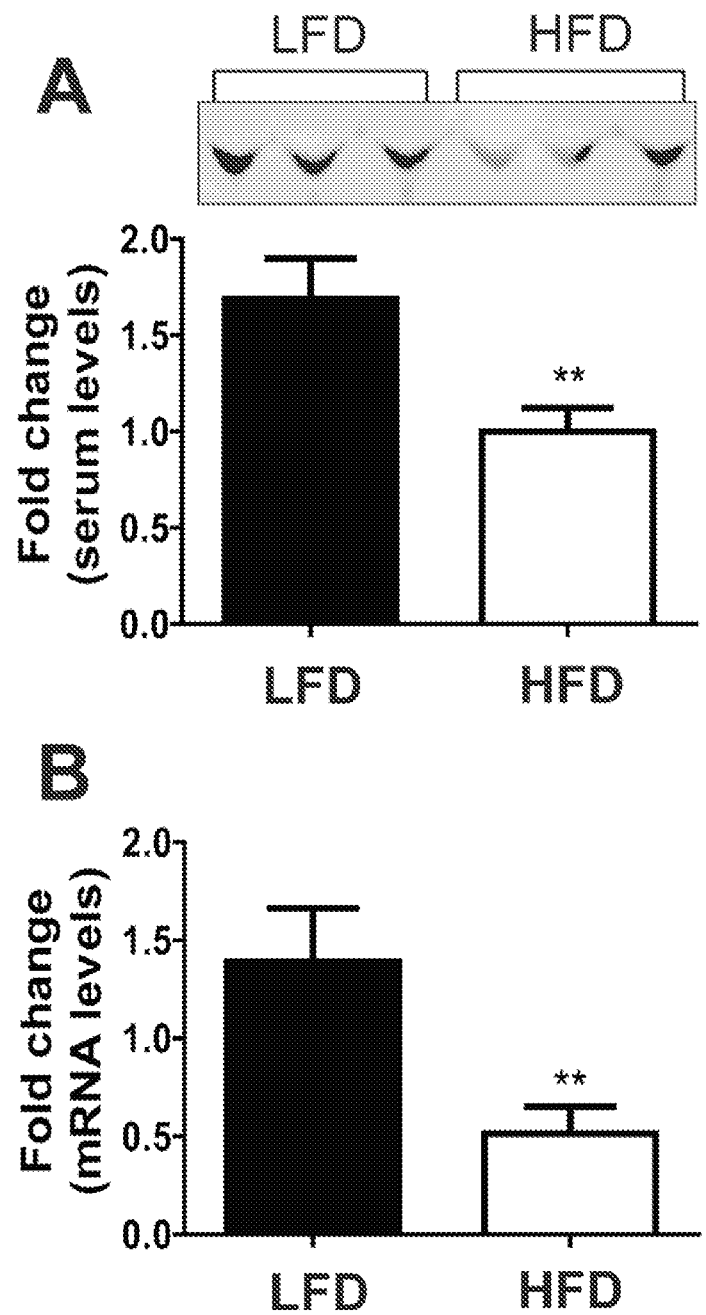
FIG. 9 depicts evidence that High-fat diet reduces myonectin expression and its circulating levels. (A) Immunoblot quantification of serum myonectin (CTRP15) levels in mice fed a high-fat diet (HFD) or an isocaloric-matched low-fat diet (LFD) for 12 weeks. (B) Quantitative PCR analysis of myonectin expression in calf muscle isolated from LFD- or HFD-fed male mice. All data are expressed as fold change (normalized to control) and shown as mean±SEM (n=8 mice/group).

Myonectin (CTRP15) protein expression and circulating levels are reduced in the obese state. To test if myonectin expression and circulating levels are responsive to long-term chronic alteration in whole-body energy balance, the mRNA and serum levels in DIO mice were examined. As compared to mice fed an isocaloric-matched low-fat diet, mice fed a high-fat diet had lower myonectin mRNA and serum levels (FIG. 9A, 9B), indicating that obesity-induced alteration in energy balance may be linked to dysregulation of myonectin-mediated processes in the obese state.

Example 9

Figure 10:
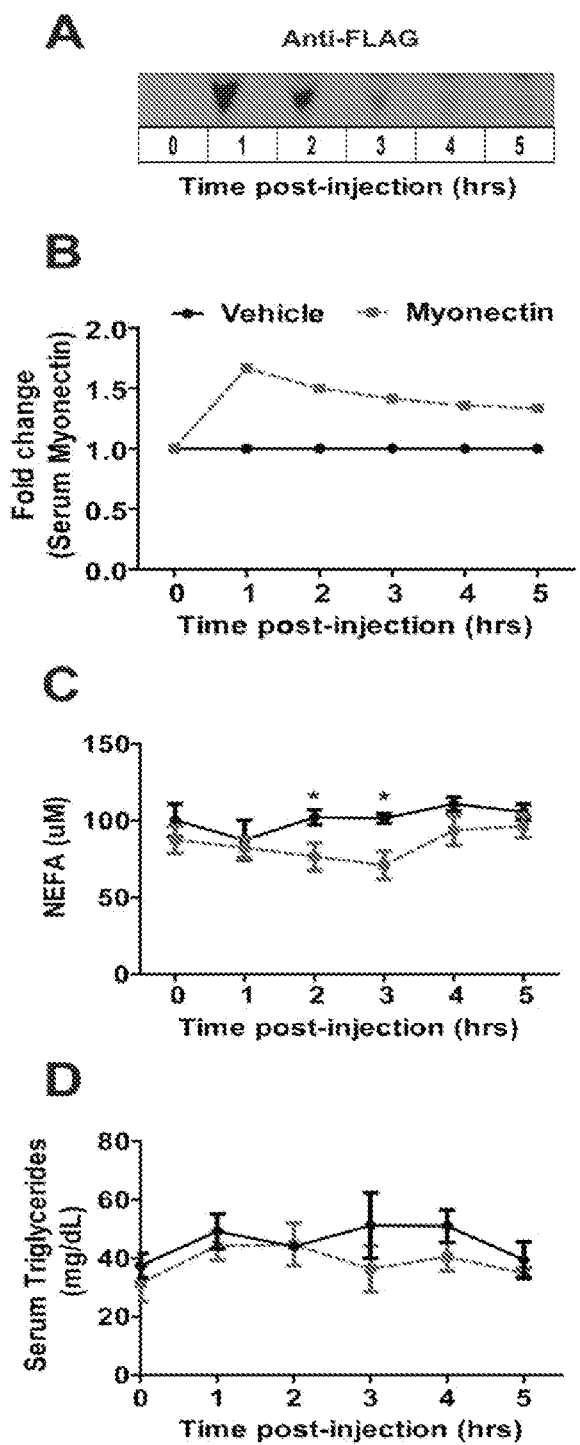
FIG. 10 shows that recombinant myonectin (CTRP15) administration reduces serum non-esterified free fatty acid (NEFA) levels in mice. (A) Immunoblot detection of FLAG epitope-tagged myonectin in mouse serum before and after recombinant protein injection. (B) Immunoblot quantification revealed a 70% elevation in serum myonectin levels above normal baseline levels after recombinant protein injection. (C-D) Male mice were injected i.p. with vehicle or myonectin (5 µg/ml) and sera were harvested every hour for 5 hours following recombinant protein administration. Food was removed 2 hours prior to protein injection. Serum non-esterified fatty acid (C) and triglyceride (D) levels were quantified (n=5 mice/group).

Recombinant myonectin (CTRP15) protein administration lowers circulating free fatty acids levels. To address the possible metabolic function of myonectin in vivo, purified recombinant myonectin was administered to wild-type male mice. Due to multiple posttranslational modifications (glycosylation and oligomerization), recombinant myonectin was produced in mammalian cells to ensure biologically active protein. When injected intraperitoneally into mice at a dose of 5 μg/g body weight, circulating levels of recombinant myonectin reached their maximum at 1 hour and gradually declined over time (FIG. 10A). At the injected dose we could raise serum levels of myonectin by 60-70% above endogenous steady-state levels (FIG. 10B). Elevating the circulating level of myonectin did not result in lowering of blood glucose over time when compared to mice injected with vehicle control (data not shown). In contrast, a relatively modest rise in serum myonectin levels was sufficient to lower (by ~30%) NEFA levels over time relative to vehicle-injected controls (FIG. 10C). However, no significant difference was observed in serum triacylglycerol levels between the two groups of mice (FIG. 10D). These data suggest a potential role of myonectin in regulating systemic fatty acid metabolism.

Example 10

Recombinant myonectin (CTRP15) protein promotes fatty acid uptake but not adipose tissue lipolysis. Myonectin can lower circulating NEFA levels via two possible mechanisms—suppressing adipose tissue lipolysis or promoting fatty acid uptake into cells. Treatment of primary adipose tissue (epididymal fat pads) ex vivo with recombinant myonectin alone did not increase lipolysis (data not shown). Isoproterenol, a potent activator of lipolysis, robustly induced adipose tissue lipolysis, but combined administration of recombinant myonectin did not further enhance isoproterenol-induced lipolysis (data not shown). Thus, the suppression of adipose tissue lipolysis is likely not the mechanism by which myonectin lowers serum NEFA levels in mice.

Figure 11:
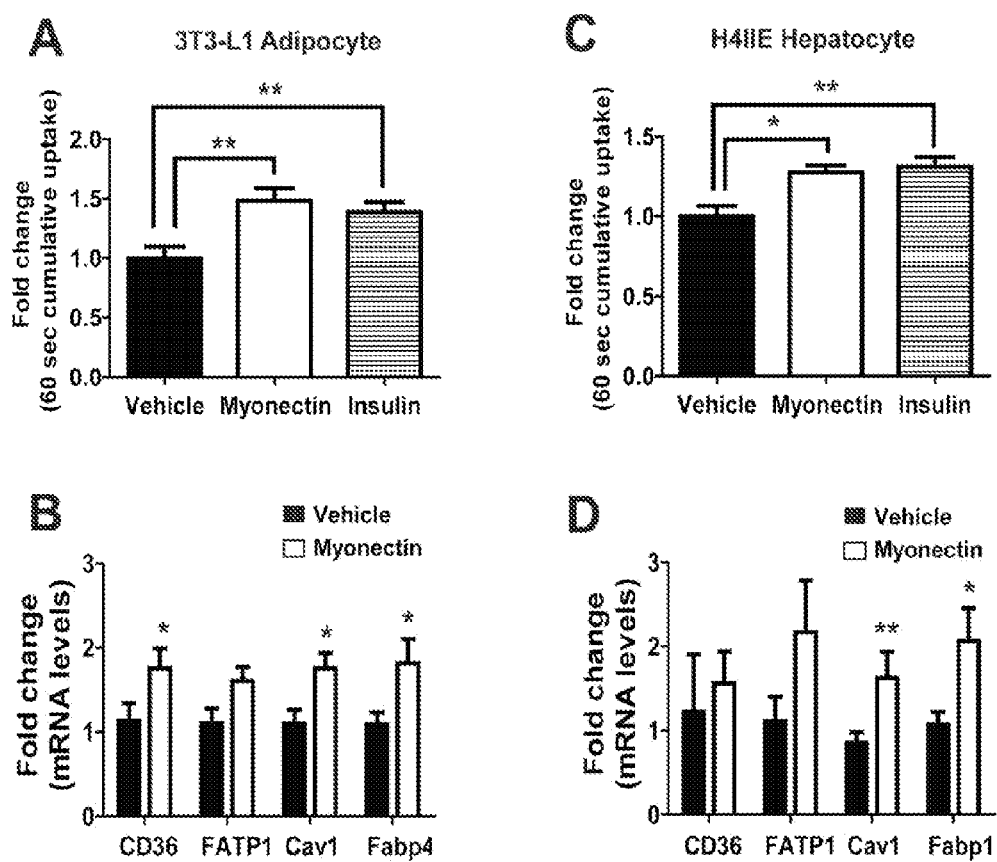
FIG. 11 depicts data showing that myonectin enhances fatty acid uptake in 3T3-L1 adipocytes and H4IIE hepatocytes via transcriptional mechanism. Mouse 3T3-L1 adipocytes (A) or rat H4IIE hepatocytes (C) were treated overnight with vehicle buffer, recombinant myonectin (5 ug/ml), or insulin (50 nM), and subject to [H]$^3$-labelled palmitate treatment for 10, 30, or 60 seconds (n=8/group). Data represents cumulative uptake over 60 seconds. (B and D) Quantitative PCR analysis of CD36, FATP1, Caveolin-1 (Cav1), and FABP4 or FABP1 expression in adipocytes (B) or hepatocytes (D) treated with vehicle buffer or recombinant myonectin (5 µg/ml) (n=8/group). All expression data were normalized to 18S rRNA. All data are expressed as fold change (normalized to control) and shown as mean±SEM.

Next, it was investigated whether myonectin promotes fatty acid uptake in differentiated mouse 3T3-L1 adipocytes. Treatment of adipocytes with a saturating dose of insulin (50 nM) led to a maximum 50% increase in fatty acid uptake (FIG. 11A). Similarly, treatment of adipocytes with recombinant myonectin (5 μg/ml) also enhanced fatty acid uptake to the same extent as insulin. While a lower dose of myonectin (2 μg/ml) resulted in a more modest increase (~20%) in lipid uptake, a higher dose of myonectin (10 μg/ml) did not further enhance lipid uptake in adipocytes beyond 50%, suggesting that 5 µg/ml likely represents a saturating dose that results in maximum lipid uptake (data not shown). Several proteins, such as CD36, FATP1, Cav1, and Fabp4, are known to play important roles in fatty acid uptake into cells. Quantitative real-time PCR analysis showed that expression of these genes was upregulated in adipocytes by recombinant myonectin (FIG. 11B). To determine whether myonectin-mediated enhancement of lipid uptake is specific to adipocytes, the effect of myonectin on lipid uptake was also tested in rat H4IIE hepatocytes. A modest (~25%) but consistent increase in fatty acid uptake into hepatocytes stimulated with myonectin (5 µg/mL) was observed, an effect similar to cells treated with a saturating dose of insulin (50 nM) (FIG. 11C). Enhanced lipid uptake is coupled to increased expression of Cav1 and Fabp1 in H4IIE hepatocytes (FIG. 11D). Together, these results indicate that myonectin promotes lipid uptake into adipocytes and hepatocytes via transcriptional up-regulation of genes involved in fatty acid uptake.

Example 11

Figure 12:
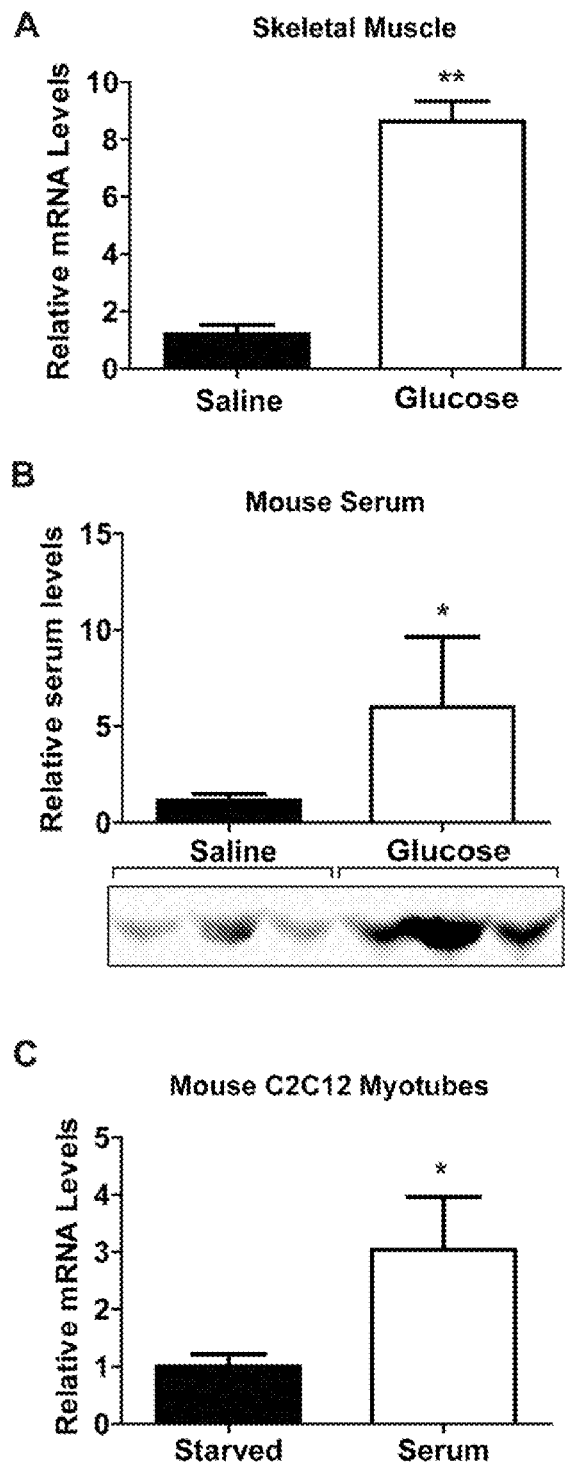
FIG. 12 depicts myonectin expression and circulating levels are reduced by starvation and increased by nutrient availability. 12A-B, Twenty-four-hour fasted mice were tail vein-injected with 10 µL/g body weight of 20% (w/v) glucose or a matched volume of saline (n=6). Skeletal muscle and sera were harvested 3 h later and subjected to quantitative real-time PCR analysis of myonectin expression (12) and immunoblot quantification of serum myonectin levels (12B). 12C, Quantitative real-time PCR analysis of myonectin expression in differentiated mouse C2C12 myotubes (n=6) treated for 18 h in DMEM containing 5 mM glucose and 0.1% BSA, with 10% Fetal Bovine Serum (FBS) (Serum) or without (Starved). All quantitative real-time PCR data were normalized to β-Actin values. *$p<0.05$; **$p<0.01$

Myonectin expression is repressed by starvation and induced by nutrient supplementation. It was previously shown that myonectin expression and circulating levels are highly upregulated in mice by re-feeding after a 12-h fast. However, a prolonged 24-h food deprivation (considered starvation in mice) is necessary to observe pronounced effects on liver autophagy (*Mol Biol Cell* 15, 1101-1111 (2004)). To evaluate changes in myonectin expression during starvation, mice were fasted for 24 h and injected with a bolus of glucose or saline. A striking increase in myonectin mRNA (~8-fold) and circulating protein levels (~5-fold) was observed when starved mice were given a bolus of glucose compared to a bolus of saline (FIG. 12 A-B). Correspondingly, myonectin mRNA expression was markedly reduced in differentiated C2C12 myotubes when cells were subjected to serum deprivation (FIG. 12 C), mimicking starvation-induced autophagy (J Biol Chem 275, 29900-29906 (200)). These results indicate that myonectin expression is repressed by starvation and induced by nutrient availability in cultured skeletal muscle cells and in mice.

Example 12

Figure 13:
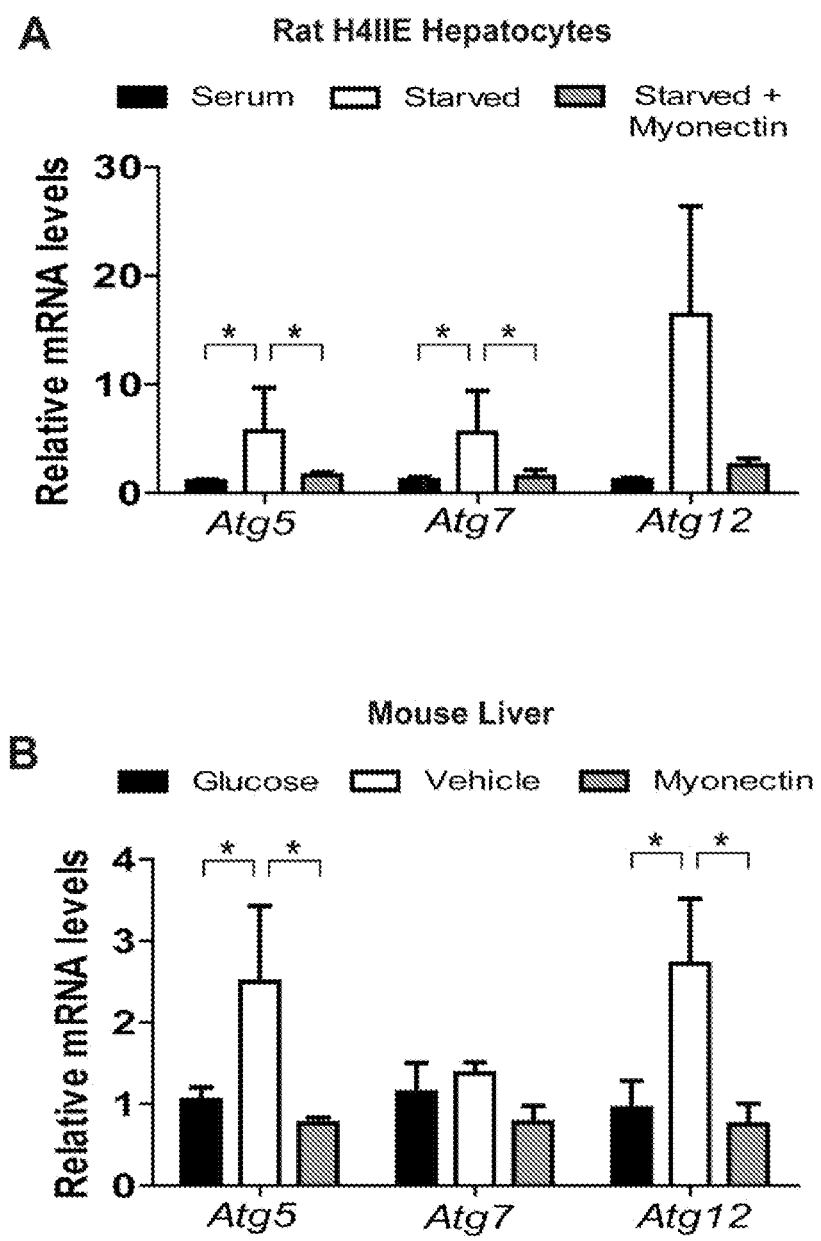
FIG. 13 shows that myonectin suppresses the expression of starvation-induced autophagy genes. 13A, Quantitative real-time PCR analysis of Atg5, Atg7, and Atg12 mRNA in H4IIE hepatocytes (n=6) cultured for 5 h in medium containing 10% FBS (Serum), Hepes buffer (Starved), or 5 ng/mL recombinant myonectin protein (Starved+ Myonectin). 13B, Mice (n=6) were fasted for 24 h and tail vein-injected with 10 µL/g body weight of 20% glucose (w/v), Hepes buffer (vehicle), or 1 µg/g body weight of recombinant myonectin protein. Four h later, livers were harvested and subjected to quantitative PCR analysis for Atg5, Atg7, and Atg12 mRNA expression. All quantitative PCR data were normalized to β-Actin values. *$p<0.05$

Myonectin suppresses the expression of autophagy genes in H4IIE hepatocytes and mouse liver. Expression of key autophagy genes in mouse liver is known to be altered in response to nutrient deprivation. Autophagy-related protein ATG7 is required for starvation-induced protein degradation in the liver, whereas ATG5 and ATG12 are critical components needed for the formation of autophagasome precursor. A strong induction of Atg5, Atg7, and Atg12 genes was observed when H4IIE hepatocytes were serum-starved for 5 h (FIG. 13A). Treatment with recombinant myonectin protein was sufficient to repress the induction of Atg genes in response to serum deprivation (FIG. 13A). To confirm our results in vivo, mice were fasted for 24 h and injected with a bolus of glucose, vehicle, or myonectin (1 µg/g body weight). Recombinant protein administration resulted in a 4-fold increase in the circulating levels of myonectin 10 min following protein injection compared to saline injection. As expected, starved mice injected with control vehicle showed a significant up-regulation of Atg5 and Atg12 expression in mouse liver, and this induction was suppressed when starved mice were given a bolus of glucose (FIG. 13B). Recombinant myonectin protein administration to starved mice also suppressed Atg5 and Atg12 induction in mouse liver to the same extent as glucose injection (FIG. 13B). These results suggest that myonectin regulates the expression of key autophagy genes in cultured hepatocytes and liver in response to nutrient availability.

Example 13

Figure 14:
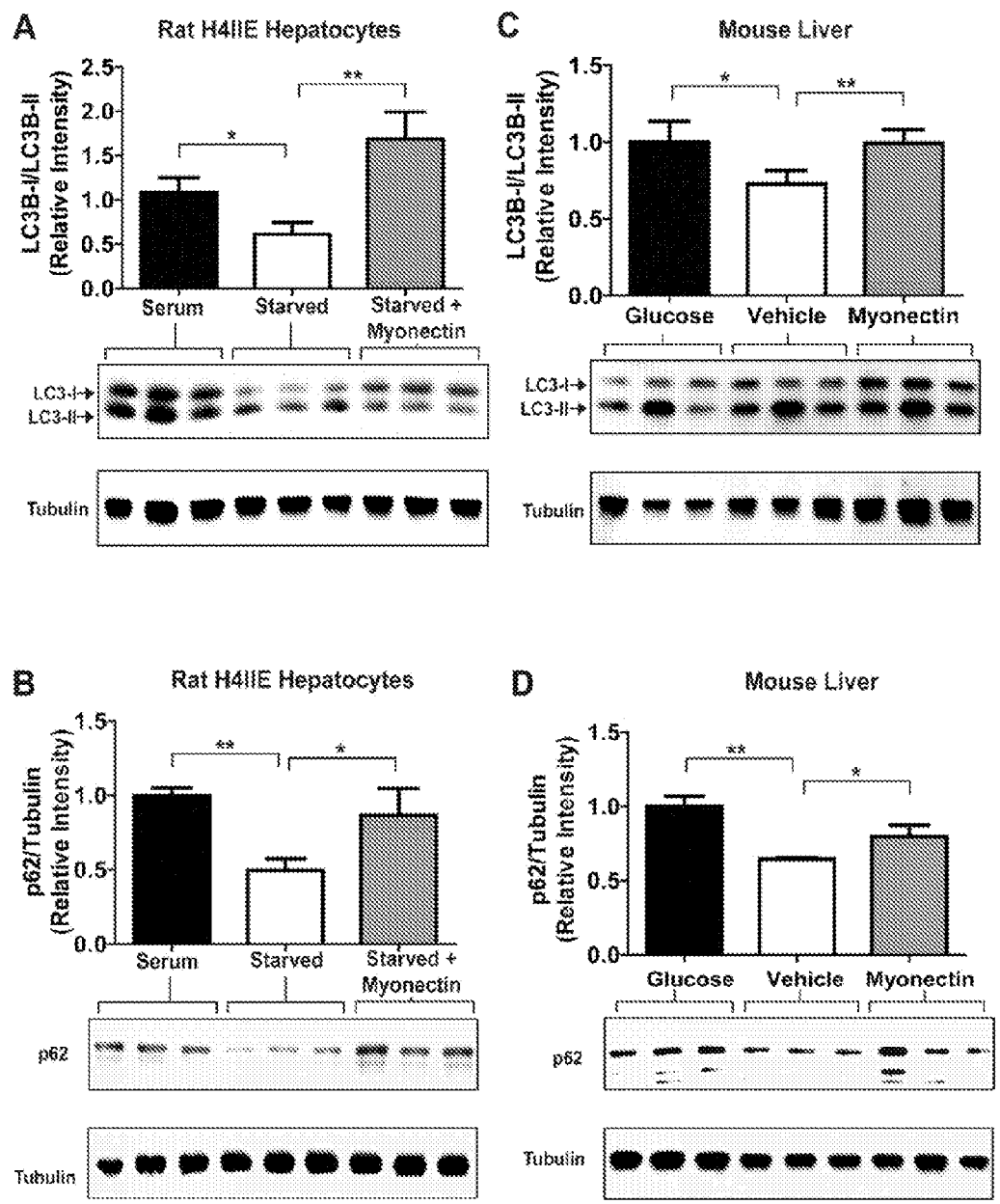
FIG. 14 illustrates that myonectin reduces autophagasome formation and autophagy-mediated p62 degradation. 14A, Immunoblot quantification of autophagy marker Light Chain 3 (LC3) in H4IIE hepatocytes cultured for 5 h in medium containing 10% FBS (Serum), Hepes buffer (Starved), or 5 µg/mL myonectin. LC3-II denotes the lipidated form of protein, observed in a slight shift in size from the non-lipidated band (LC3-I). 14B, Immunoblot quantification of p62 in H4IIE hepatocytes cultured for 24 h in medium containing 10% FBS (Serum), Hepes buffer (Starved), or 5 µg/mL myonectin. 14C-D, Mice (n=6) were fasted for 24 h and tail vein-injected with 10 µL/g body weight of 20% glucose (w/v), Hepes buffer (vehicle), or 1 µg/g body weight of recombinant myonectin protein. Four h later, livers were harvested and subjected to immunoblot quantification of LC3 (14C) and p62 (14D). All blots show tubulin as the loading control. *$p<0.05$; $p<0.01$

Myonectin inhibits LC3 lipidation and autophagasome-dependent p62 degradation. Lipidation of microtubule associated protein-1 light chain 3 (LC3) is a critical initial step in autophagy, leading to subsequent aggregation and autophagasome formation. These autophagasomes contain p62/SQSTM1 protein complexes, which are eventually degraded by cellular autophagy. Thus, the ratio of non-lipidated to lipidated LC3 and p62 degradation serve as markers for early and late stages of autophagy, respectively. H4IIE hepatocytes deprived of serum for 5 h activated autophagy, as indicated by a marked decrease (~50%) in the proportion of non-lipidated (indicated by LC3-I) to lipidated (indicated by LC3-II) forms of LC3 when compared to cells cultured in the presence of serum (FIG. 14A). Cells administered recombinant myonectin protein potently suppressed the initiation of autophagy to the same extent as cells cultured in the presence of serum, as indicated by the complete abolishment of starvation-induced increase in LC3 lipidation (ratio of LC3-I/LC3-II) (FIG. 14A).

To assess late-stage autophagasome-dependent protein degradation, H4IIE hepatocytes were cultured for 24 h in the presence of serum, serum-starved, or serum-starved in the presence of recombinant myonectin protein, and probed for p62 protein levels. As expected, serum starvation significantly reduced the total protein levels of p62 relative to cells cultured in the presence of serum (FIG. 14B). Recombinant myonectin protein treatment essentially reversed this process in starved cells, as indicated by the complete inhibition of starvation-induced p62 degradation (FIG. 14B). To ensure that effects of myonectin on cellular autophagy are physiologically relevant in vivo, we subjected mice to a 24-h fast, then administered a bolus of glucose, vehicle, or recombinant myonectin protein. Consistent with our in vitro results, starved mice injected with vehicle control activated autophagy, as indicated by significantly greater LC3 lipidation and p62 degradation in the liver compared to starved mice injected with a bolus of glucose (FIG. 14C, D). Importantly, myonectin administration largely suppressed starvation-induced LC3 lipidation and p62 degradation in the liver, to an extent similar to glucose administration (FIG. 14C, D). These results indicate that myonectin inhibits early-stage autophagasome formation, as well as late-stage autophagy-dependent p62 degradation in vitro and in vivo.

Example 14

Figure 15:
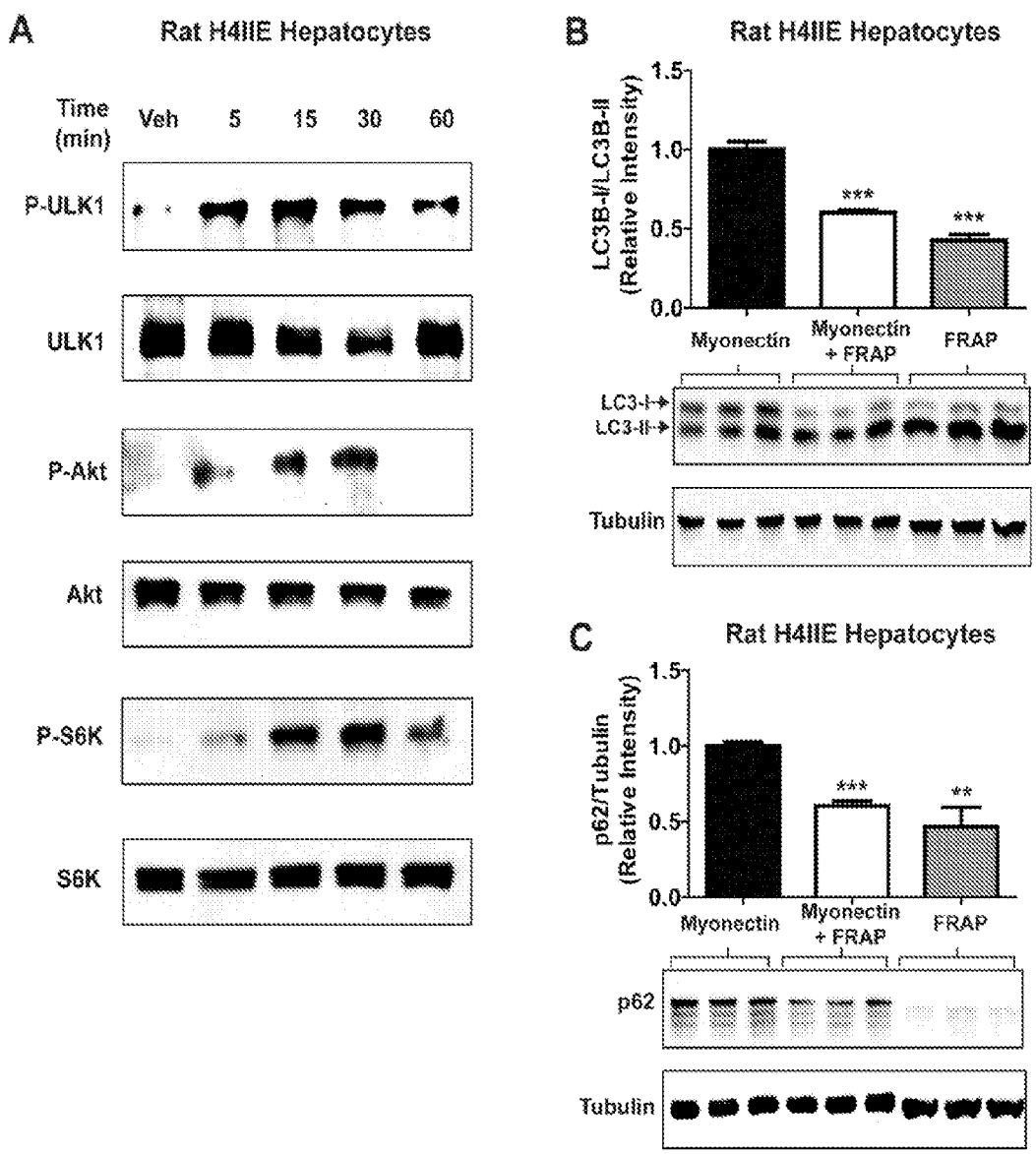
FIG. 15 depicts that myonectin activates Akt/mTOR/S6 Kinase pathway in H4IIE hepatocytes. 15A, H4IIE hepatocytes were serum-starved for 2 h, then placed in DMEM containing 5 mM glucose and myonectin (5 µg/mL) or vehicle (Hepes buffer) for 5, 15, 30, or 60 min Immunoblots were probed for phospho-ULK1 (Ser757) (P-ULK1), ULK1, phospho-Akt (Thr308) (P-Aid), Akt, phospho-p70 S6 Kinase (Thr389) (P-S6K), and p70 S6 Kinase (S6K). B-C, H4IIE hepatocytes (n=6) were serum starved in the presence of myonectin (5 µg/mL), FRAP (10 ng/mL), or both for 5 h and immunoblotted for LC3-I and II (15B), or 24 h and probed for p62 (15C). Tubulin is shown as the loading control. $p<0.01$; ***$p<0.001$

Myonectin activates the Akt/mTOR pathway to suppress autophagy. We next investigated what signaling pathways are activated by myonectin in cells to block autophagy. H4IIE hepatocytes were serum-starved for 1 h to reduce background signaling, then treated with vehicle control or recombinant myonectin protein for 5, 15, 30, or 60 min. Relative to vehicle-treated cells, myonectin dramatically induced the phosphorylation of three key autophagy-regulatory enzymes (FIG. 15A). Phosphorylation of UNC-51-like kinase 1 (ULK1) at Ser-757 disrupts its association with AMP-activated protein kinase (AMPK) and abolishes AMPK-mediated autophagasome formation. Myonectin robustly induced phosphorylation of Ser-757 on ULK1. In addition, myonectin also induced the phosphorylation and activation of protein kinase B/Akt (Thr-308) and p70 S6 kinase (Thr-389) (FIG. 15A). Activation of Akt and p70 S6 kinase elicits an mTORC1-dependent suppression of cellular autophagy.

Example 15

Inhibition of mTOR signaling abrogates myonectin ability to suppress autophagy. To confirm that myonectin acts via the Akt/mTOR pathway to inhibit autophagy, H4IIE hepatocytes were treated with recombinant myonectin protein in the presence or absence of FRAP (a potent rapamycin analog) to pharmacologically inhibit mTOR function. Serum-starved cells treated with vehicle and FRAP activated autophagy, as indicated by greater LC3 lipidation and p62 degradation, and these processes were suppressed by myonectin treatment (FIG. 15B, C). FRAP completely abolished the ability of myonectin to inhibit starvation-induced LC3 lipidation and greatly reduced its ability to prevent p62 degradation when simultaneously given to cells (FIG. 15B, C).

Figure 16:
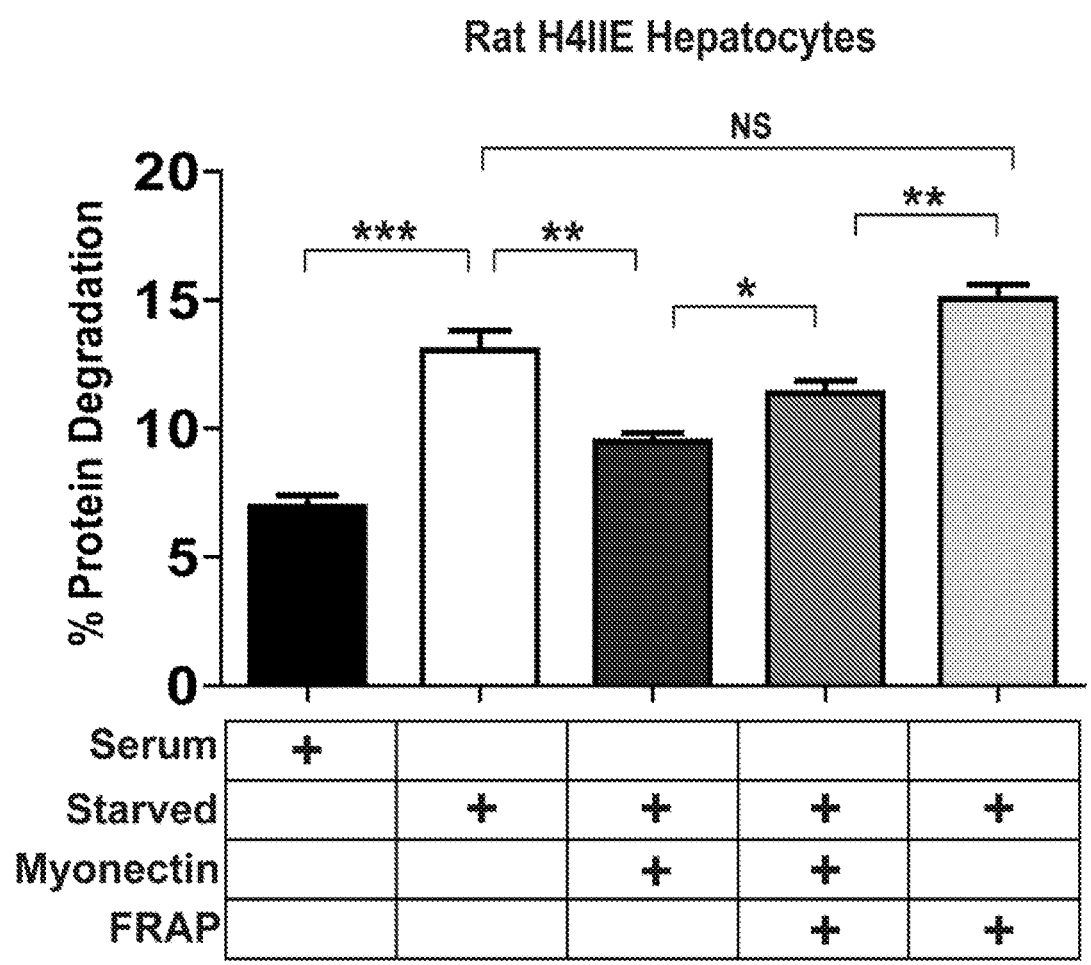
FIG. 16 shows that inhibition of mTOR signaling abolishes ability of myonectin to suppress autophagy in hepatocytes. The rate of degradation of 14C-valine-labeled, long-lived proteins was measured in H4IIE hepatocytes (n=6) cultured in glucose-free medium (starved), or glucose-free medium containing 10% FBS (Serum), myonectin (5 µg/mL), FRAP (10 ng/mL), or myonectin plus FRAP. *$p<0.05$; $p<0.01$; *$p<0.001$

LC3 lipidation and p62 degradation represent are useful and informative markers for early and late stage of autophagy. However, to functionally verify our results, we used a biochemical assay to quantify the degradation of long-lived proteins in cells when autophagy is fully engaged. To do so, H4IIE hepatocytes were pulsed with $^{14}$C-labeled valine to radiolabel intracellular proteins before subjecting the cells to starvation. As expected, serum-starved cells had a ~2-fold higher level of total bulk protein degradation compared to cells cultured in the presence of serum (FIG. 16). Recombinant myonectin protein treatment largely abolished starvation-induced protein degradation. No significant differences were observed between cells starved in the presence or absence of FRAP, indicating that mTOR inhibition does not further enhance autophagy upon serum deprivation. FRAP treatment, however, substantially inhibited the ability of myonectin to suppress starvation-induced cellular protein degradation (FIG. 16). These results show that myonectin modulates cellular autophagy via the Akt/mTOR signaling pathway.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of lowering circulating serum fatty acid levels in a subject, comprising administering to the subject an effective amount of C1q tumor necrosis factor (TNF) related protein 15 (CTRP15) myonectin protein or a functional portion thereof, and a pharmaceutically acceptable carrier, wherein the functional portion is the C1q/TNF-like domain of the CTRP15 myonectin protein.

2. A method of increasing fatty acid uptake in adipocytes or hepatocytes in a subject, comprising administering to the subject an effective amount of CTRP15 myonectin protein or a functional portion thereof, and a pharmaceutically acceptable carrier, wherein the functional portion is the C1q/TNF-like domain of the CTRP15 myonectin protein.

* * * * *

SEQUENCE LISTING

<160> NUMBER OF SEQ ID NOS: 32

<210> SEQ ID NO 1
<211> LENGTH: 2835
<212> TYPE: DNA
<213> ORGANISM: mus musculus

<400> SEQUENCE: 1

```
aaggcgccga cctgaccagc cgtgctcttt actgccgccg ccgccgccag catggcctcg        60
acccgccgcc ccgtcggagc tcgcacgctg ctcgcctgcg ccagcctact cgccgccatg       120
ggcctcggtg tccctgagtc cgcggagccc gtggggactc atgcacgccc gcagccgccc       180
ggggccgagc tgcccgcccc gccagccaac agcccgccgg aacccaccat tgcgcatgca       240
cacagtgtgg atccccggga tgcttggatg ctgttcgtca agcagagtga caagggggatc       300 aacagtaaga ggaggagcaa agccaggagg ctgaagcttg gcctgccagg accccaggg        360 ccaccaggtc ctcagggccc cccaggcccc tttatcccat ctgaggttct gctgaaggag       420
ttccagctgt tgctgaaagg cgcagtacgg cagcgagaga gccatctgga gcactgcacc       480
agggatctca ctacaccagc ctcgggtagc ccttcccgtg tcccagccgc ccaggagctt       540
```

```
gatagccagg acccaggggc attgttagct ctgctggctg cgaccttggc ccagggcccg      600
cgggcaccac gtgtggaggc cgcattccac tgtcgcttgc gccgggatgt gcaggtggat      660
cggcgtgcgt tgcacgagct tgggatctac tacctgcccg aagttgaggg agccttccac      720
cggggcccag gcttgaatct gaccagcggc cagtacaccg cacctgtggc tggcttctat      780
gcgcttgctg ccactctgca cgtggcactc accgagcagc caagaaaggg accaacacga      840
ccccgggatc gtctgcgcct gctgatctgc atccagtctc tctgccagca caatgcctcc      900
ctggagactg tgatggggct ggagaacagc agcgagctct tcaccatctc agtaaatggt      960
gtcctctatc tacaggcagg acactacact tctgtcttct tggacaatgc cagcggctcc     1020
tccctcacgg tacgcagtgg ctctcacttc agtgctatcc tcctgggcct gtgagcagct     1080
gctgcaggct cttacccctta ccaagcagag tggtgacagt ggccctgtgc aaggaagc      1140 ccactggacc tctgcacaca ctggccatcg caatacctct taccatagcc actgtattcc     1200
tgcagaggtg atggaagcag gctctcccag aaccagcagc aatttgtgaa tatcctaagc     1260
cctgcttggc tcttctggga ccatccagct tacatggtag cacttgctct attcccagct     1320
acagagctgg catccttgta gctctattca ggctcaaatt ccttcctgtg cccagcaaa      1380 ctagtcaggc cactcactac ctgggacaac tcagcctgca cagggtagga aatgactgta     1440
ggtccttagt gcttaagagg gaagcccaga ccttcttgga ccatacactg tctacctggg     1500
ttcctgagtt cctatcctgc agtattctct atgtctgcct agagtacagc ctcagggacc     1560
taggaacgtc aggggccagt aatcctaggc ctggcagcag tttctgtgtc tggggtaagc     1620
acgatgacct gcaggcccct ggtgagcacc ctaacatact ggagctacac tcctttgcca     1680
tccttatcct ctacaaaggc taccagccaa cttcccaacc ctcggaggct cgggctcact     1740
gctagggccc acacactaaa ccaaagtttg agcacagtta tccacacagg gcacctgctc     1800
acaagtttcc ctcctgagac tccattgtaa aggggtggg tggtctggct gaatggcagc      1860
ttgggaggaa gaagctggct gagggctctt cccatgagaa gggctgccac cctgcagcct     1920
gctttagtgg ttttcccatt tttaacaaaa tgtgggacca gatcctaata ggcagtggag     1980
agggctggac cttccaagtc ctgatggcct gctgatgaaa gagctgacag ccagcagtcc     2040
acacccacca gctgctttgg gatctcttgg cctagcagga gtgctcaagc ctgggacaga     2100
ggggatagct ccagttgctt catctttcag ctgacaccag gatgaagcta ccacatcaga     2160
acgcccttct ataatcggac ctgtccccaa atcaggcttc caacagagcg acaggtgcct     2220
gggggagctg tccgtgagca ggcctggccc gattctcagt atggctggta cccaccctac     2280
caggaagcac tgtgctggcc tgggtcctga ctccctggca ctctgataag gacatgaggt     2340
ggaaacaccc caccctttc tggatttcat tttgtatcca gtgggcacag acatgtcagt      2400
gacgttatct tctacccttg agaaagccac ataagcacat atcttacctt ccaacaactg     2460
tgttacacag caacttaaaa gtatttattg tgtcatattg ctaggcagaa tatatttatg     2520
taatggatca cacaaagccc taacaatgaa gggcagaccc gagaagcatg acctctttcc     2580
agctcacttc accaaagacc atgagggta agctctggaa agcaagggag aaatgccttt      2640
agtcttgaga ctcctactga agtagcagga gaggctctta ctaaccagga aggccacagt     2700
gccaagagtt acccagacag aagcacttgg ggacatgggt cacagcctat ggggcactga     2760
atgattcctg ggctgctatg aaattgctaa attaaactgt ttagctttct gatgaaaaaa     2820
aaaaaaaaaa aaaaa                                                      2835
```

<210> SEQ ID NO 2
<211> LENGTH: 340
<212> TYPE: PRT
<213> ORGANISM: mus musculus

<400> SEQUENCE: 2

Met Ala Ser Thr Arg Arg Pro Val Gly Ala Arg Thr Leu Leu Ala Cys
1               5                   10                  15

Ala Ser Leu Leu Ala Ala Met Gly Leu Gly Val Pro Glu Ser Ala Glu
            20                  25                  30

Pro Val Gly Thr His Ala Arg Pro Gln Pro Pro Gly Ala Glu Leu Pro
        35                  40                  45

Ala Pro Pro Ala Asn Ser Pro Pro Glu Pro Thr Ile Ala His Ala His
    50                  55                  60

Ser Val Asp Pro Arg Asp Ala Trp Met Leu Phe Val Lys Gln Ser Asp
65                  70                  75                  80

Lys Gly Ile Asn Ser Lys Arg Arg Ser Lys Ala Arg Arg Leu Lys Leu
                85                  90                  95

Gly Leu Pro Gly Pro Pro Gly Pro Gly Pro Gln Gly Pro Pro Gly
            100                 105                 110

Pro Phe Ile Pro Ser Glu Val Leu Leu Lys Glu Phe Gln Leu Leu Leu
        115                 120                 125

Lys Gly Ala Val Arg Gln Arg Glu Ser His Leu Glu His Cys Thr Arg
    130                 135                 140

Asp Leu Thr Thr Pro Ala Ser Gly Ser Pro Ser Arg Val Pro Ala Ala
145                 150                 155                 160

Gln Glu Leu Asp Ser Gln Asp Pro Gly Ala Leu Leu Ala Leu Leu Ala
                165                 170                 175

Ala Thr Leu Ala Gln Gly Pro Arg Ala Pro Arg Val Glu Ala Ala Phe
            180                 185                 190

His Cys Arg Leu Arg Arg Asp Val Gln Val Asp Arg Arg Ala Leu His
        195                 200                 205

Glu Leu Gly Ile Tyr Tyr Leu Pro Glu Val Glu Gly Ala Phe His Arg
    210                 215                 220

Gly Pro Gly Leu Asn Leu Thr Ser Gly Gln Tyr Thr Ala Pro Val Ala
225                 230                 235                 240

Gly Phe Tyr Ala Leu Ala Ala Thr Leu His Val Ala Leu Thr Glu Gln
                245                 250                 255

Pro Arg Lys Gly Pro Thr Arg Pro Arg Asp Arg Leu Arg Leu Leu Ile
            260                 265                 270

Cys Ile Gln Ser Leu Cys Gln His Asn Ala Ser Leu Glu Thr Val Met
        275                 280                 285

Gly Leu Glu Asn Ser Ser Glu Leu Phe Thr Ile Ser Val Asn Gly Val
    290                 295                 300

Leu Tyr Leu Gln Ala Gly His Tyr Thr Ser Val Phe Leu Asp Asn Ala
305                 310                 315                 320

Ser Gly Ser Ser Leu Thr Val Arg Ser Gly Ser His Phe Ser Ala Ile
                325                 330                 335

Leu Leu Gly Leu
            340

<210> SEQ ID NO 3
<211> LENGTH: 32
<212> TYPE: DNA
<213> ORGANISM: Mus musculus

```
<400> SEQUENCE: 3
cagcatggcc tcgacccgcc gccccgtcgg ag                          32

<210> SEQ ID NO 4
<211> LENGTH: 24
<212> TYPE: DNA
<213> ORGANISM: mus musculus

<400> SEQUENCE: 4
cagctgctgc aggctcttac cctt                                   24

<210> SEQ ID NO 5
<211> LENGTH: 8
<212> TYPE: PRT
<213> ORGANISM: artificial sequence
<220> FEATURE:
<223> OTHER INFORMATION: synthetic

<400> SEQUENCE: 5

Asp Tyr Lys Asp Asp Asp Asp Lys
1               5

<210> SEQ ID NO 6
<211> LENGTH: 9
<212> TYPE: PRT
<213> ORGANISM: artificial sequence
<220> FEATURE:
<223> OTHER INFORMATION: synthetic

<400> SEQUENCE: 6

Tyr Pro Tyr Asp Val Pro Asp Tyr Ala
1               5

<210> SEQ ID NO 7
<211> LENGTH: 17
<212> TYPE: PRT
<213> ORGANISM: artificial sequence
<220> FEATURE:
<223> OTHER INFORMATION: synthetic

<400> SEQUENCE: 7

Lys Gln Ser Asp Lys Gly Ile Asn Ser Lys Arg Arg Ser Lys Ala Arg
1               5                   10                  15

Arg

<210> SEQ ID NO 8
<211> LENGTH: 21
<212> TYPE: DNA
<213> ORGANISM: artificial sequence
<220> FEATURE:
<223> OTHER INFORMATION: synthetic

<400> SEQUENCE: 8
tgcttggatg ctgttcgtca a                                      21

<210> SEQ ID NO 9
<211> LENGTH: 21
<212> TYPE: DNA
<213> ORGANISM: artificial sequence
<220> FEATURE:
<223> OTHER INFORMATION: synthetic

<400> SEQUENCE: 9
cagatgggat aaagggcct g                                       21
```

<210> SEQ ID NO 10
<211> LENGTH: 21
<212> TYPE: DNA
<213> ORGANISM: Artificial sequence
<220> FEATURE:
<223> OTHER INFORMATION: Synthetic

<400> SEQUENCE: 10
ggcaccacac cttctacaat g                                    21

<210> SEQ ID NO 11
<211> LENGTH: 21
<212> TYPE: DNA
<213> ORGANISM: Artificial sequence
<220> FEATURE:
<223> OTHER INFORMATION: Synthetic

<400> SEQUENCE: 11
ggggtgttga aggtctcaaa c                                    21

<210> SEQ ID NO 12
<211> LENGTH: 18
<212> TYPE: DNA
<213> ORGANISM: Artificial sequence
<220> FEATURE:
<223> OTHER INFORMATION: Synthetic

<400> SEQUENCE: 12
atctggcacc acaccttc                                        18

<210> SEQ ID NO 13
<211> LENGTH: 17
<212> TYPE: DNA
<213> ORGANISM: Artificial sequence
<220> FEATURE:
<223> OTHER INFORMATION: Synthetic

<400> SEQUENCE: 13
agccaggtcc agacgca                                         17

<210> SEQ ID NO 14
<211> LENGTH: 21
<212> TYPE: DNA
<213> ORGANISM: Artificial sequence
<220> FEATURE:
<223> OTHER INFORMATION: Synthetic

<400> SEQUENCE: 14
tgtgcttcga gatgtgtggt t                                    21

<210> SEQ ID NO 15
<211> LENGTH: 22
<212> TYPE: DNA
<213> ORGANISM: Artificial sequence
<220> FEATURE:
<223> OTHER INFORMATION: Synthetic

<400> SEQUENCE: 15
accaacgtca aatagctgac tc                                   22

<210> SEQ ID NO 16
<211> LENGTH: 20
<212> TYPE: DNA
<213> ORGANISM: Artificial sequence
<220> FEATURE:

<223> OTHER INFORMATION: Synthetic

<400> SEQUENCE: 16
ccctccagaa gaaaatggat                                           20

<210> SEQ ID NO 17
<211> LENGTH: 20
<212> TYPE: DNA
<213> ORGANISM: Artificial sequence
<220> FEATURE:
<223> OTHER INFORMATION: Synthetic

<400> SEQUENCE: 17
atagctcaga tgctcgctca                                           20

<210> SEQ ID NO 18
<211> LENGTH: 20
<212> TYPE: DNA
<213> ORGANISM: Artificial sequence
<220> FEATURE:
<223> OTHER INFORMATION: Synthetic

<400> SEQUENCE: 18
cctgcacaac accaacacac                                           20

<210> SEQ ID NO 19
<211> LENGTH: 21
<212> TYPE: DNA
<213> ORGANISM: Artificial sequence
<220> FEATURE:
<223> OTHER INFORMATION: Synthetic

<400> SEQUENCE: 19
cacctgactt tatggcttcc c                                         21

<210> SEQ ID NO 20
<211> LENGTH: 21
<212> TYPE: DNA
<213> ORGANISM: Artificial sequence
<220> FEATURE:
<223> OTHER INFORMATION: Synthetic

<400> SEQUENCE: 20
tgtcagcctg gcatttgata a                                         21

<210> SEQ ID NO 21
<211> LENGTH: 21
<212> TYPE: DNA
<213> ORGANISM: Artificial sequence
<220> FEATURE:
<223> OTHER INFORMATION: Synthetic

<400> SEQUENCE: 21
tcactcatgt cccagatctc a                                         21

<210> SEQ ID NO 22
<211> LENGTH: 21
<212> TYPE: DNA
<213> ORGANISM: Artificial sequence
<220> FEATURE:
<223> OTHER INFORMATION: Synthetic

<400> SEQUENCE: 22
tggcctcgga acagttgttt a                                         21

```
<210> SEQ ID NO 23
<211> LENGTH: 21
<212> TYPE: DNA
<213> ORGANISM: Artificial sequence
<220> FEATURE:
<223> OTHER INFORMATION: Synthetic

<400> SEQUENCE: 23
gggcaaagga ctgattcaca t                                          21

<210> SEQ ID NO 24
<211> LENGTH: 18
<212> TYPE: DNA
<213> ORGANISM: Artificial sequence
<220> FEATURE:
<223> OTHER INFORMATION: Synthetic

<400> SEQUENCE: 24
ttcggttgca gtttcgcc                                              18

<210> SEQ ID NO 25
<211> LENGTH: 21
<212> TYPE: DNA
<213> ORGANISM: Artificial sequence
<220> FEATURE:
<223> OTHER INFORMATION: Synthetic

<400> SEQUENCE: 25
ccatgcctgt gatttgcagt a                                          21

<210> SEQ ID NO 26
<211> LENGTH: 23
<212> TYPE: DNA
<213> ORGANISM: Artificial sequence
<220> FEATURE:
<223> OTHER INFORMATION: Synthetic

<400> SEQUENCE: 26
cgactggagc aggaggacac tga                                        23

<210> SEQ ID NO 27
<211> LENGTH: 26
<212> TYPE: DNA
<213> ORGANISM: Artificial sequence
<220> FEATURE:
<223> OTHER INFORMATION: Synthetic

<400> SEQUENCE: 27
ggacactgac atggactgaa ggagta                                     26

<210> SEQ ID NO 28
<211> LENGTH: 27
<212> TYPE: DNA
<213> ORGANISM: Artificial sequence
<220> FEATURE:
<223> OTHER INFORMATION: Synthetic

<400> SEQUENCE: 28
cttgccattg acaccttgt cactctg                                     27

<210> SEQ ID NO 29
<211> LENGTH: 28
<212> TYPE: DNA
<213> ORGANISM: Artificial sequence
<220> FEATURE:
<223> OTHER INFORMATION: Synthetic
```

```
<400> SEQUENCE: 29
cttcagcagc gcctcgggtg ggatgatg                                28

<210> SEQ ID NO 30
<211> LENGTH: 25
<212> TYPE: DNA
<213> ORGANISM: Artificial sequence
<220> FEATURE:
<223> OTHER INFORMATION: Synthetic

<400> SEQUENCE: 30
cgcacctttc agcagcagct ggaac                                   25

<210> SEQ ID NO 31
<211> LENGTH: 28
<212> TYPE: DNA
<213> ORGANISM: Artificial sequence
<220> FEATURE:
<223> OTHER INFORMATION: Synthetic

<400> SEQUENCE: 31
ggcggcagag gaaagcggcc tccacgcg                                28

<210> SEQ ID NO 32
<211> LENGTH: 28
<212> TYPE: DNA
<213> ORGANISM: Artificial sequence
<220> FEATURE:
<223> OTHER INFORMATION: Synthetic

<400> SEQUENCE: 32
gtgcagcgcg cgccgctcca ccaacgcg                                28
```